United States Patent [19]
Gifford

[11] Patent Number: 5,750,335
[45] Date of Patent: May 12, 1998

[54] SCREENING FOR GENETIC VARIATION

[75] Inventor: David K. Gifford, Weston, Mass.

[73] Assignee: Massachusetts Institute of Technology, Cambridge, Mass.

[21] Appl. No.: 52,157

[22] Filed: Apr. 22, 1993

Related U.S. Application Data

[63] Continuation-in-part of Ser. No. 874,192, Apr. 24, 1992, abandoned.

[51] Int. Cl.⁶ .............................. C12Q 1/68; C12P 19/34; C07K 14/195; C07K 17/00
[52] U.S. Cl. .............................. 435/6; 435/91.2; 435/810; 536/25.4; 530/350; 530/412; 530/810; 935/77; 935/78
[58] Field of Search .............................. 435/6, 5, 91, 810; 536/23.1, 25.4; 935/77, 78; 530/810, 412, 350

[56] References Cited

U.S. PATENT DOCUMENTS

| | | | |
|---|---|---|---|
| 4,535,058 | 8/1985 | Weinberg et al. | 435/6 |
| 4,556,643 | 12/1985 | Paau et al. | 436/501 |
| 4,725,537 | 2/1988 | Fritsch et al. | 435/6 |
| 4,794,075 | 12/1988 | Ford et al. | 435/6 |
| 5,045,450 | 9/1991 | Thilly et al. | 435/6 |
| 5,459,039 | 10/1995 | Modrich | 435/6 |

FOREIGN PATENT DOCUMENTS

| | | |
|---|---|---|
| 0 265 244 A3 | 4/1988 | European Pat. Off. |
| 0 407 789 A1 | 1/1991 | European Pat. Off. |
| 0 412 883 A1 | 2/1991 | European Pat. Off. |
| WO 90/13668 | 1/1991 | WIPO |
| WO 91/00925 | 1/1991 | WIPO |
| WO 91/13075 | 9/1991 | WIPO |
| WO 93/02216 | 2/1993 | WIPO |

OTHER PUBLICATIONS

Blackwell et al., "Differences and Similarities in DNA-Binding Preferences of MyoD and E2A protein Complexes Revealed by Binding Site Selection", Science, vol. 250, pp. 1104–1110, 1990.

Cotton, "Detection of Single Base Changes in Nucleic Acid", Advances in Geome Biology, vol. 1, pp. 253–300, 1991.

Hochuli et al., "Genetic Approach to Facilitate Purificaiton of Recombinant Proteins with a Novel Metal Chelate Absorbent", Bio/Technology, Nov. 1988, pp. 1321–1325.

The FLAG Biosystem, International Biotechnologies, Inc., 1991.

McKay, "Binding of a Simian Virus 40 T Antigen–related Protein to DNA", J. Mol. Biol. (1981) 145, pp. 471–488.

(List continued on next page.)

Primary Examiner—Carla J. Myers
Attorney, Agent, or Firm—Testa, Hurwitz & Thibeault, LLP

[57] ABSTRACT

Disclosed is a method of genetic screening for a nucleotide variation, the method including the steps of (A) providing a mixture of nucleic acids comprising heteroduplex nucleic acids and excess homoduplex nucleic acids, wherein each said heteroduplex comprises a test nucleic acid strand isolated from an organism and a reference nucleic acid strand, each said heteroduplex also comprising a mismatched nucleotide pair, wherein said excess homoduplex nucleic acids are generated by reannealing of a first test or reference nucleic acid strand with a fully complementary second test or reference nucleic acid strand; (B) subjecting said mixture to a mismatch binding protein under conditions which promote binding to form a heteroduplex/binding protein complex; and C) detecting the presence of said mismatched nucleotide pair as an indication of the presence of genetic variation between said test and reference nucleic acids.

70 Claims, 10 Drawing Sheets

OTHER PUBLICATIONS

Mankovich et al., "Nucleotide Sequence of the *Salmonella typhimurium* mutL Gene Required for Mismatch Repair: Homology of MutL to HexB of *Streptococcus pneumoniae* and to PMS1 of the Yeast *Saccharomyces Cerevisiae*", J. Bacteriol., Oct. 1989, vol. 171, No. 10 pp. 5326–5331.

Protein Fusion and Purification System, New England Biolabs Catalog, 1990–1991, pp. 68–69.

Potter et al., "A 'Southern Cross' Method for the Analysis of Genome Organization and the Localization of Transcription Units", Gene, 48 (1986) pp. 229–239.

Yokota et al., "Differential Cloning of Genomic DNA: Cloning of DNA with an Altered Primary Structure by in–gel Competitive Reassociation", Proc. Natl. Acad. Sci., USA, vol. 87, pp. 6398–6402, Aug. 1990.

Vershon et al., "Isolation and Analysis of Arc Repressor Mutants: Evidence for an Unusual Mechanism of DNA Binding", Proteins: Structure, Function, and Genetics, 1:302–311 (1986).

Kinzler et al., "Whole Genome PCR: Application to the Identification of Sequences Bound by Gene Regulatory Proteins", vol. 17, No. 10, (1989), pp. 3645–3653.

Lisitsyn et al., "Cloning the Differences Between Two Complex Genomes", Science, vol. 259, (1993) pp. 946–951.

Su et al., "*Escherichia coli* mutS–encoded Protein Binds to Mismatched DNA Base Pairs", Proc. Natl. Acad. Sci. USA, vol. 83, pp. 5057–5061, Jul. 1986.

Harber, "Genetic and Biochemical Analyses of the *Salmonella typhimurium* MutS Mismatch Repair Protein", (1990) pp. 1–96.

Affinity Chromatography, Pharmaeia LKB Biotechnology Catalog, 1992, pp. 72–104.

Pang et al., "Identification and Characterization of the mutL and mutS Gene Products of *Salmonella typhimurium* LT2", J. Bacteriol., Sep. 1985, pp. 1107–1015, vol. 163, No. 3.

Cotton, "Detecting of Single Base Changes in Nucleic Acid", JAI Press 1991.

Stephenson et al., "Selective Binding to DNA Base Pair Mismatches by Proteins from Human Cells", The Journal of Biological Chemistry, (1989) vol. 264, No. 35, pp. 21177–21182.

Jiricny et al., "A Human 200–kDa Protein Binds Selectively to DNA Fragments Containing GT Mismatches", Proc. Natl. Acad. Sci. USA, vol. 85, pp. 8860–8864, Dec. (1988).

Modrich, "Mechanisms and Biological Effects of Mismatch Repair", Annu. Rev. Genet. (1991) 25:229–53.

Jiricny et al., "Mismatch–containing oligonucleotide duplexes bound by the *E. coli* mutS–encoded protein", vol. 16, No. 16 (1988), pp. 7843–7853.

Roberts et al., "Detection of Novel Genetic Markers by Mismatch Analysis", vol. 17, No. 15 (1989) pp. 5961–5971.

Cotton G.H., (1989) "Detection of Single Base Changes in Nucleic Acids", Biochemical Journal 263:1–10.

Su et al. J. Biol Chem (1988) 6829–6835.

McKay, J. Molec Biol (1981) 145: 471–488.

Hochuli et al, Bio/Technology (1988) 1321–1325.

Saihi et al, Proc Natl Acad Sci, USA, (1989) 86: 6230–6234.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..49
        ( D ) OTHER INFORMATION: /note= "DKG-MUTS5T PRIMER"

( x i ) SEQUENCE DESCRIPTION: SEQ ID NO:1:

CGGAATTCGC ATCATCATCA TCATCATATG AATGAGTCAT TTGATAAGG     49

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..30
        ( D ) OTHER INFORMATION: /note= "DKG-MUTS3X PRIMER"

( x i ) SEQUENCE DESCRIPTION: SEQ ID NO:2:

CGCGGATCCT TACACCAGAC TTTTCAGCCG     30

( 2 ) INFORMATION FOR SEQ ID NO:3:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..31
        ( D ) OTHER INFORMATION: /note= "SRB-5-G"

( x i ) SEQUENCE DESCRIPTION: SEQ ID NO:3:

AGAAGTAGAC GTCCAGCTGC CTAGTCTACA G     31

( 2 ) INFORMATION FOR SEQ ID NO:4:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature ( B ) LOCATION: 1..31
        ( D ) OTHER INFORMATION: /note= "SRB-3-T"

( x i ) SEQUENCE DESCRIPTION: SEQ ID NO:4:

CTGTAGACTA GGCAGTTGGA CGTCTACTTC T                    31

( 2 ) INFORMATION FOR SEQ ID NO:5:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..31
        ( D ) OTHER INFORMATION: /note= "SRB-3-C"

( x i ) SEQUENCE DESCRIPTION: SEQ ID NO:5:

CTGTAGACTA GGCAGCTGGA CGTCTACTTC T                    31

( 2 ) INFORMATION FOR SEQ ID NO:6:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..28
        ( D ) OTHER INFORMATION: /note= "ARC5-1"

( x i ) SEQUENCE DESCRIPTION: SEQ ID NO:6:

CCGGCGGATG AAAGGAATGA GCAAAATG                        28

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..21
        ( D ) OTHER INFORMATION: /note= "ARC3-5"

( x i ) SEQUENCE DESCRIPTION: SEQ ID NO:7:

GGCTTCAACT TTACGCGCCA A                               21

SCREENING FOR GENETIC VARIATION

This application is a continuation-in-part of U.S. Ser. No. 07/874,192, filed Apr. 24, 1992, now abandoned.

The invention relates to the detection of sequence differences between test and reference nucleic acids; that is, to means and methods for the detection of the existence in a test polynucleotide of a genetic defect, or variation, from a reference, typically wild-type, polynucleotide. The invention is useful in clinical, forensic, and research contexts.

BACKGROUND OF THE INVENTION

Methods known in the art for comparing nucleotide sequence differences in DNA molecules are reviewed in Cotton, R., 1989, Biochem. J. 263:1, and include those aimed at detecting sequence differences when the sequence and location of a given region of DNA are known, discovering previously unknown mutations in a known region of DNA, and locating a previously unknown region containing a mutation.

Previous methods of detecting known sequence differences include: the failure of an oligonucleotide having a wild-type DNA sequence to hybridize under stringent conditions to sample DNA containing a mutation, the failure of PCR primers to hybridize under stringent conditions to sample DNA containing a mutation, and the consequent failure of sample DNA containing a mutation to become amplified using PCR; the failure of adjacent oligonucleotides to ligate due to a failure of one or both oligonucleotides to hybridize under stringent conditions to sample DNA containing a mutation; the use of primer extension analysis to detect incorporation of differentially labeled bases where the primer hybridizes to the sample DNA adjacent to the mutation; and the detection of changes in cleavability of a restriction enzyme site as an indicator of the presence of a mutation.

Previous methods of detecting a mutation of unknown identity within a known region of the genome include those in which a heteroduplex molecule is created from one strand of test DNA and one strand of reference DNA. Mismatches between the reference and test DNAs may be detected by carbodiimide modification of mismatched Thymidine (T) and Guanine (G) bases and detection of the resultant mobility shifts of modified versus control DNA; by ribonuclease cleavage of mismatched pyrimidine bases of RNA/DNA hybrids, and detection of points of cleavage in the molecule; by detection of differences in melting temperature between heteroduplex and homoduplex DNA, e.g., by denaturing gel electrophoresis; and chemical modification and cleavage of mismatched bases using hydroxylamine (to modify cytosine) or osmium tetroxide (to modify thymidine) modification and piperidine cleavage, and subsequent detection of cleaved DNA. Additional methods for detecting an unknown mutation within a region of DNA include: detecting differences in secondary structure by looking for differential mobility in gels of single stranded reference and test DNA; and by direct sequencing of both reference and test DNAs.

Several methods of locating mutations where both the identity and region of the mutation are described in the art. RFLP analysis, in which Restriction Fragment Length Polymorphisms are analyzed, identifies sequence differences which occur at restriction enzyme cleavage sites of test and reference DNAs, or by the insertion or deletion of a number of bases. RFMP analysis (Gray, 1992, Amer. J. Hum. Genet. 50:331) is a variation of RFLP analysis in which denaturing gradient gel electrophoresis is used to identify sequence variations both at and between restriction enzyme cleavage sites.

The Southern Cross method, described in Potter and Dressler (1986, Gene 48:229), also depends upon sequence differences between test and reference DNAs that occur at sites of restriction enzyme cleavage. In this method, a reference DNA is digested with one or more restriction enzymes and analyzed by a modified Southern procedure. According to this modified Southern procedure, hybridization of two identical membranes, which are positioned at 90° angles with respect to each other, gives a signal that forms along a diagonal line of hybridization. In contrast, where test and reference membranes are hybridized at 90° angles, differences in restriction fragment patterns between the test and reference DNAs are indicated by off-diagonal signals.

Finally, the differential genomic DNA cloning method depends upon the inability of dephosphorylated reference DNA in a reference/test DNA hybrid to ligate to dephosphorylated vector DNA. In this method, described in Yokata and Oihsi (1990, Proc. Nat. Aca. Sci. 87:6398), test and reference DNAs are digested separately with restriction enzymes, reference DNA is then dephosphorylated, and the two DNAs are combined at a ratio of 100/1 of reference to test DNA. The mixture is subjected to agarose gel electrophoresis, and the DNA is denatured and renatured in the gel, such that unique restriction fragments will likely self-anneal and non-unique fragments will likely reanneal with reference strands. Subsequent cloning of the reannealed fragments will favor reannealed test DNA clones, since the dephosphorylated reference DNA or reference/test hybrids will not be ligated to a dephosphorylated vector.

DNA mispairing can occur in vivo and is recognized and corrected by repair proteins. Mismatch repair has been studied most intensively in *E. coli*, *Salmonella typhimurium*, and *S. pneumoniae*. The MutS, MutH and MutL proteins of *E. coli* are involved in the repair of DNA mismatches, as is the product of the uvrD gene in *E. coli*, helicase II. MutS appears to play a central role in mismatch correction. Besides the repair system directed by Dam-mediated methylation of d(GATC) sites, MutS is also active in two other less efficient mismatch repair processes. One of these processes acts on symmetrically methylated DNA and may serve to repair mismatches produced during recombination. The other corrects cytosine (C) to Thymidine (T) transitions at the internal C of the Dcm methylase sequence d(CCA/TGG) or subsets thereof and also requires mutL$^+$ and dcm$^+$.

Mismatched base pairs can arise in vivo during homologous recombination of allelic genes, by chemical modification of DNA, or from errors made by DNA polymerase. Repair of mismatched DNA base pairs has been invoked to explain a variety of genetic phenomena, including gene conversion in Neurospora spp. and other fungi (Mitchell, 1955, Proc. Nat. Aca. Sci. 41:215; Rossignol, 1969, Genetics 63:795), postmeiotic segregation in *Saccharomyces cerevisiae* (Williamson et al., 1985, Genetics 110:609), high negative interference and gene conversion in lambda phage crosses (Nevers et al., 1975, Mol. Gen. Genet. 139:233; White et al., 1974, Proc. Nat. Aca. Sci. 71:1544; Wildenberg et al., 1975, Proc. Nat. Aca. Sci. 72:2202), and the existence of high and low efficiency transforming markers in *Streptococcus pneumoniae* (Ephrussi et al., 1966, J. Gen. Physiol. 49:211; Lacks, 1966, Genetics 53:207).

Jiricny et al. (1988, Nucl. Ac. Res. 16:7843) performed in vitro binding experiments using MutS and a series of synthetic DNA duplexes containing known mismatches or mismatch analogues of the purine/pyrimidine type in order to demonstrate that MutS binds in vitro to double-stranded DNA containing a mismatched nucleotide pair. Su et al. (1986, Proc. Nat. Aca. Sci. 83:5057) have shown that highly purified MutS binds to a purified 120 base pair restriction fragment containing a single mismatch in vitro and protects approximately 22 nucleotides surrounding the mismatch against DNase attack. Su et al. (1988, J. Biol. Chem. 263:6829) demonstrates that MutS recognizes all eight possible DNA base mismatches.

McKay (1981, J. Mol. Biol. 145:471, hereby incorporated by reference), describes a method of purifying certain SV40 DNA restriction fragments using an immunoprecipitation procedure in which the SV40 T antigen-related protein binds to these DNA fragments. Blackwell and Weintraug (1990, Science 250:1104), hereby incorporated by reference, describes a method of purifying DNA sequences that bind to a protein of interest based on amplification of a binding site. The protein of interest is bound to DNA fragments and the bound fragment(s) is isolated using an electrophoretic mobility shift assay.

Objects of the invention include methods for rapid and accurate genetic screening and diagnosis by comparing two nucleic acids for differences in their nucleotide sequences. Another object is to diagnose genetic diseases in mammals, especially humans, by rapid screening for a previously observed mutation(s) known to cause a genetic disease. Another object is to rapidly screen the genome of an individual for genetic variation of a specific region of DNA, where the nature and position of the variation is unknown, by comparing a nucleic acid sequence known to reflect normal gene function with a nucleic acid sample suspected to contain a genetic defect. Yet another object is to locate previously unknown mutations of a nucleotide sequence and to identify the sequence itself, where the nature and position of the mutation within a region of the genome is unknown, and where the location of the region itself is unknown.

SUMMARY OF THE INVENTION

The invention provides methods of detecting and/or identifying polynucleotide sequence differences which may be the basis for genetic disease. The method involves hybridizing a "test", i.e., a potential variant, nucleic acid, e.g., from a patient, with a nucleic acid standard. If the test and standard (reference) nucleic acids contain one or more nucleotide sequence differences, then the double stranded nucleic acid formed from hybridization of the sequences will contain one or more nucleotide pair mismatches, i.e., will comprise a heteroduplex. In accordance with the invention, protocols are provided which permit detection of the presence of the heteroduplex, and/or segregation of a fraction rich in heteroduplex. The detection and fractionation methods involve exploitation of the selective binding properties of mismatch binding proteins.

The invention encompasses methods which allow for detection of differences between nucleotide sequences with greatly increased sensitivity. The methods of the invention allow one to detect single or multiple nucleotide differences between a nucleic acid standard and a sample nucleic acid without relying on restriction fragment length differences. The invention also provides for enrichment of heteroduplex fragments containing mismatches, even in a sample containing excess homoduplex, thereby achieving more sensitive detection of the mismatch. The methods also may be used quantitatively to determine the fraction of heteroduplex fragments in a mixture, and the proportion of mismatch binding protein bound to heteroduplex, and thus also may be used to determine the number of mismatches within a test sample. The methods also allow for recovery of nucleic acid fragments containing sequence mismatches from a mixture containing excess fully complementary fragments. Recovered fragments may be analyzed further, for example, to determine the identity and position of the mismatch by determining the nucleotide sequence of the mismatch region.

In a first aspect, the invention features methods of genetic screening for a nucleotide variation which generally include the following steps. A mixture of nucleic acids which includes heteroduplex nucleic acids, i.e., heteroduplex including a test nucleic acid strand hybridized with a reference nucleic acid strand generated by annealing test and reference nucleic acid, and which includes a mismatched nucleotide pair, is subjected to a mismatch binding protein under conditions which promote binding of the protein to heteroduplex in the mixture to form a heteroduplex/binding protein complex. The presence of the mismatched nucleotide pair then is detected, using the methods disclosed below, as an indication of the presence of genetic variation between the test and reference nucleic acids.

In preferred embodiments of this aspect of the invention, the mixture provided may be a complex mixture of different nucleic acid fragments, some of which are heteroduplex fragments, but many or a majority of which are homoduplex nucleic acids. The test nucleic acid may be isolated from a collection of organisms and may include nucleic acid from any tissue or cell of several members of a species. Alternatively, the test nucleic acid may be sampled from an individual and thus may comprise nucleic acid from one unique representative of a species. In addition, the test nucleic acid may be suspected, but not known, to contain a nucleotide variation from a wild-type sequence which encodes a normal, functional protein or regulatory element. A nucleotide variation in the test nucleic acid comprises one half of a mismatched nucleotide pair when the test nucleic acid is hybridized to the reference nucleic acid.

The mixture of nucleic acids provided in the method typically are generated by annealing the test and reference nucleic acids. The test nucleic acid may be produced by cleaving double stranded test nucleic acid into a fragment which spans the same nucleotide region(s) as the reference nucleic acid(s). Both the test and reference nucleic acids may be either single or double stranded. If either is double stranded, the test mixture must be "melted", i.e., denatured to produce single stranded polynucleotide, before annealing. Generally, the test and the reference nucleic acids may be genomic DNA, cDNA, MRNA, synthetic polynucleotide, mitochondrial DNA, amplified or circular DNA, or other single or double stranded polynucleotide, from whatever source. While it is preferable that the reference nucleic acid be single stranded, it also may be double stranded.

The annealed mixture of test and reference nucleic acids will include a concentration of heteroduplexes if this test nucleic acid embodies at least one base difference from the reference. The heteroduplexes present in this mixture may be fractionated from the mixture by affinity purification in which a mismatch binding protein binds to the heteroduplexes preferentially to the homoduplexes in the mixture. The bound heteroduplexes may then be recovered from the affinity purification, e.g., released, to produce a fraction which contains a higher concentration of heteroduplex.

The methods of genetic screening also may include the immobilization of reference nucleic acid to a solid support.

For example, reference nucleic acids may be immobilized to a solid surface in a array of plural, spaced-apart spots. The spots of reference nucleic acid are then exposed separately under hybridizing conditions to a test nucleic acid such that the test and immobilized reference nucleic acids are able to form a hybrid. The hybrids then are contacted with the mismatch binding protein under conditions sufficient to allow the binding protein to bind to a heteroduplex containing a mismatched nucleotide pair. Finally, the bound mismatch binding protein, or the heteroduplex/protein complex, is detected as an indication of genetic variation between the test sample and the reference nucleic acid at that spot.

Detection of the heteroduplex may be conducted by detecting the mismatch binding protein that is bound to the heteroduplex, e.g., using a labeled form of the mismatch binding protein or a separate binding protein such as an antibody specific for the mismatch binding protein. Alternatively, the heteroduplex may be detected by detecting the complex, e.g., with an antibody specific for an epitope on the heteroduplex/mismatch binding protein complex. Alternatively, the bound mismatch binding protein or bound heteroduplex may be released from the complex before detection of the released component. Alternatively, the mismatch binding protein may modify the heteroduplex before it releases, and the modification may be subsequently detected. The heteroduplex itself can include a detectable moiety, e.g., a radioactive or other label bound to the reference nucleic acid, and the detecting step can include detecting the detectable moiety after fractionation of the heteroduplex. The methods may also include, in addition to detecting the presence of a mismatched nucleotide pair, determining the identity or location of the nucleotide variation in the test strand. The identity or location of the nucleotide variation may be determined by analyzing the nucleotide sequence of the test nucleic acid strand and comparing it to the sequence of the reference strand.

In a second aspect, the invention features methods of selectively enriching a nucleic acid preparation in fragments containing a nucleotide variation, by enriching for heteroduplex nucleic acids in a mixture. Selective heteroduplex enrichment of a mixture which includes a first concentration of heteroduplex nucleic acids may be performed by separating the heteroduplex nucleic acids by affinity purification in which the mismatch binding protein binds to heteroduplex, and recovering heteroduplex to produce a mixture that contains a second, higher concentration of heteroduplex. As a variation on this method, the mixture first is reacted with a mismatch binding protein such that the heteroduplex binds to the protein to form a heteroduplex protein complex, and then the complex is separated from the mixture by affinity purification to produce a mixture having a higher concentration of heteroduplex. In both variations of this aspect of the invention, the affinity purification step involves a binding reaction in which the heteroduplex is selectively bound by a mismatch binding protein which preferably is coupled to a solid support, followed by elution. The binding and elution steps may be repeated interactively until a desired degree of purification of heteroduplexes is achieved. Numerous modifications of this general procedure are encompassed by the invention. For example, the mismatch binding protein/heteroduplex complex may be bound by 1) a protein specific for one or both components of the complex, e.g., an antibody, 2) a metal column capable of binding to a histidine tail engineered onto the mismatch binding protein, or 3) a protein capable of binding to a flag sequence on the mismatch binding protein. A solid support may not be preferable; e.g., an antibody may be used to immunoprecipitate the mismatch binding protein/ heteroduplex complex.

In both aspects of the invention, the test nucleic acids may be prepared by, for example, performing a polymerase chain reaction on a region of interest in test nucleic acid sample. In addition, an amplification step, e.g., by polymerase chain reaction, may be useful at other points of the methods, e.g., after affinity purification of heteroduplex nucleic acids to produce an amplified heteroduplex sample. Where a PCR step is performed, it may be necessary to ligate PCR tails to the test, reference, or heteroduplex nucleic acids prior to the mismatch binding protein binding reaction.

In both aspects of the invention, when the reference nucleic acid is labeled, the methods may include the additional step of adding excess unlabeled nucleic acid to the mixture of test and reference nucleic acids to serve as a competitor to mismatch binding protein binding, thereby to reduce background. Background may be caused by the nonspecific binding of mismatch binding protein to homoduplex nucleic acid. In this case, detection of labeled reference nucleic acid does not correlate directly with the amount of heteroduplex present, even though purification was conducted with mismatch binding protein because of nonspecific interactions between the mismatch binding protein and homoduplex nucleic acid. However, the presence of unlabeled competitor creates a dilution effect on labeled homoduplex nucleic acid, formed by annealing of reference/ reference strands or test/test strands, which otherwise would be mistaken for heteroduplex. Alternatively, background may be reduced using an amplification step. PCR tails are ligated to the test and reference nucleic acids but not to the competitor nucleic acid. Excess competitor is added to the mixture prior to binding of mismatch binding protein. The subsequent amplification of presumed heteroduplex nucleic acid purified from the complex also will result in amplification of nonspecifically bound homoduplex nucleic acid. However, the presence of excess competitor nucleic acid lacking PCR tails will dilute out the effect of nonspecific binding because nonspecifically bound competitor nucleic acid will not be amplifiable.

In another aspect, the invention features apparatus for conducting comparisons of the sequence of test and reference nucleic acid, and for determining the existence or nature of a difference between two or more nucleic acid sequences. Broadly, these apparatus include, as essential elements, a mismatch binding protein, and either or both means for detecting the presence of the protein or a protein/ heteroduplex complex, and/or means for separating heteroduplex from homoduplex in a mixture.

A kit for detecting a heteroduplex nucleic acid as an indication of genetic variation may include an array of separately spaced reference nucleic acids coupled to a support, and a mismatch binding protein. Preferably, the mismatch binding protein is labeled, but alternatively, the kit may include a protein that binds the mismatch binding protein, e.g., a labeled protein such as an antibody or an unlabeled antibody that is bound by a labeled antibody. The protein capable of binding the mismatch binding protein may be immobilized on a solid support.

A detection kit may also include a mismatch binding protein immobilized on a solid support, and means for detecting a heteroduplex bound to the support through the protein, or eluted from the support.

The invention also features a kit for separating a heteroduplex nucleic acid from a mixture of heteroduplex and homoduplex nucleic acids, which includes a mismatch binding protein, a moiety capable of binding a mismatch binding protein, or a moiety capable of binding a complex comprising a mismatch binding protein and a heteroduplex, all coupled to a solid support, and means for separating the heteroduplex from homoduplex. Any of the kits may include a reference nucleic acid.

In still another aspect, the invention features a solid support, e.g., an affinity matrix for binding heteroduplex nucleic acids. The support comprises a mismatch binding protein coupled to a high surface area matrix. Alternatively, the support may comprise immobilized moieties which bind a mismatch binding protein, or bind a heteroduplex/mismatch binding protein complex.

As used herein, a "mismatch binding protein" refers to any organic moiety, e.g., a protein, polypeptide, organic analog thereon, or other moiety or mixture of moieties, which bind preferentially to regions of double-stranded nucleic acids containing a mismatch. The mismatched regions may be as little as one nucleotide pair and may be as large as 5–10 nucleotide pairs, e.g., a small loop region. Such binding proteins include but are not limited to naturally occurring proteins, such as MutS, MutL, MutH, and MutU (helicase II) from *E. coli* and *Salmonella typhimurium*, HexA and HexB from *S. pneumonaie*, and mismatch binding proteins found in higher organisms, including humans (Jiricny et al., 1988 Proc. Nat. Aca. Sci. U.S.A. 85:8860; Stephenson et al., 1989, J. Biol. Chem. 264:21177), and analogs thereof which contain amino acid differences that do not destroy binding of the protein to the mismatched nucleotides, but may have properties not present in conventional mismatch binding protein, e.g., thermostability. As used herein, "mismatch binding protein" also includes proteins which do not naturally bind a nucleotide mismatch, but which has been altered or engineered to bind a nucleic acid fragment containing mismatched nucleotides, and muteins, derivatives, truncated analogs, or species variants of naturally occurring mismatch binding proteins. The definition also includes an antibody or a mixture of antibodies that recognizes and binds heteroduplex nucleic acids. Also included in the invention are mismatch binding proteins that modify nucleic acids containing mismatches, thus allowing the nucleic acid to be subsequently recognized by other proteins or means.

As used herein, "homoduplex" refers to double stranded nucleic acid containing first and second strands which are fully complementary. "Heteroduplex" refers to double stranded nucleic acid containing first and second strands which are substantially complementary, but which contains regions of noncomplementary, i.e., one or more mismatched nucleotide pairs. Regions of noncomplementarity may cause small loops to form within one strand of the heteroduplex. There may be as few as one region of noncomplementary per heteroduplex, or many regions, so long as the heteroduplex can form a stable hybrid under conditions selected to-form the hybrid. A non-complementary region may include insertions or deletions of one or more bases of one strand relative to the other strand. "Competitor" nucleic acid refers to homoduplex nucleic acid that is either unlabeled or does not contain PCR tails, or that is distinguishable from heteroduplex nucleic acid. "Excess homoduplex" nucleic acid refers to a mixture containing at least two-fold, preferably at least five- or ten-fold, and most preferably at least 100-fold more homoduplex nucleic acid than heteroduplex nucleic acid, where the excess homoduplex nucleic acid is a natural by-product of the process that created the heteroduplex nucleic acid. "Excess competitor" nucleic acid refers to a mixture containing at least two-fold, preferably at least five- or ten-fold, most preferably at least 100-fold more competitor homoduplex-nucleic acid than heteroduplex nucleic acid. "Nucleic acid" refers to DNA or RNA containing naturally occurring nucleotides or synthetic substitutions thereof. "Test" nucleic acid refers to single- or double-stranded DNA or RNA to be compared to the nucleic acid standard, e.g., DNA from a patient suspect of having a genetic disease. "Reference nucleic acid" refers to a single or double-stranded nucleic acid standard, e.g., a nucleic acid encoding a normal protein or regulatory function. "Mismatched nucleotide pair" refers to a nucleotide pair which does not match according to Watson/Crick base pairing, i.e., is not G:C, A:T, or A:U. A "nucleotide variation" is a nucleotide sequence difference between a test nucleic acid and a reference nucleic acid, and constitutes as little as one base pair of a mismatched nucleotide pair. "Amplify" means to make multiple copies of a nucleic acid fragment or a mixture of nucleic acids. "PCR" means polymerase chain reaction, and "PCR tail" refers to oligoxucleotide duplexes which are ligated to the ends of nucleic acids and which, upon denaturation, may hybridize to complementary primers used to prime the synthesis of DNA. "Labeled" means containing a detectable moiety or a moiety which participates in a reactions resulting in detection, e.g., a chromogenic reaction. A detectable moiety may, include but is not limited to a radioactive marker, e.g., $^{32}P$, and non-radioactive markers, e.g., biotin. "Affinity purification" or "affinity fractionation" means to separate heteroduplex or heteroduplex/binding protein complex from other components based on the affinity of the heteroduplex or complex. An "affinity matrix" is a solid support which is used to affinity purify heteroduplex or heteroduplex/binding protein complex.

As used herein, a nucleic acid "isolated from an organism" refers to DNA or RNA that has been extracted directly from cells or tissue of one or more members of a species, e.g., prokaryotic, eukaryotic, or mammalian, especially human DNA or RNA from human cells or tissue; or to DNA that has been cloned from genomic DNA or from RNA sequences; or to DNA that has been amplified from an organism's DNA using the technique of polymerase chain reaction. Nucleic acid "native, to an individual" refers to DNA or RNA that has been extract from, cloned from, or amplified from cells or tissue of a member of a species. Where a nucleic acid is "suspected to contain" a nucleotide variation, it is not known whether the nucleic acid contains the variation prior to performing the method of the invention.

Other features and advantages of the invention will be apparent from the following description of the preferred embodiments, from the drawing, and from the claims.

DETAILED DESCRIPTION OF THE INVENTION

We first briefly describe the drawings.

Drawings

Figure 1:
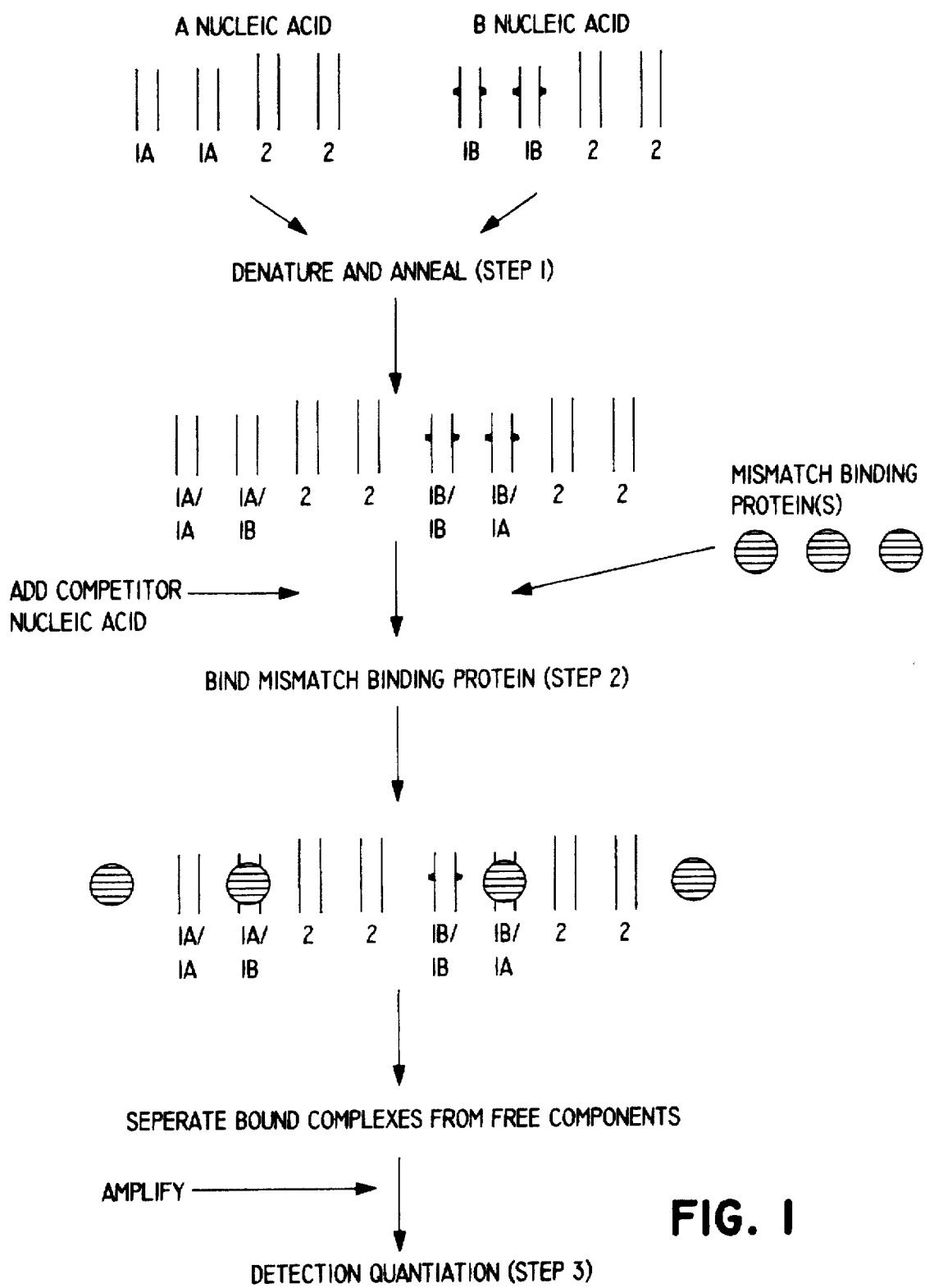
Figure 2:
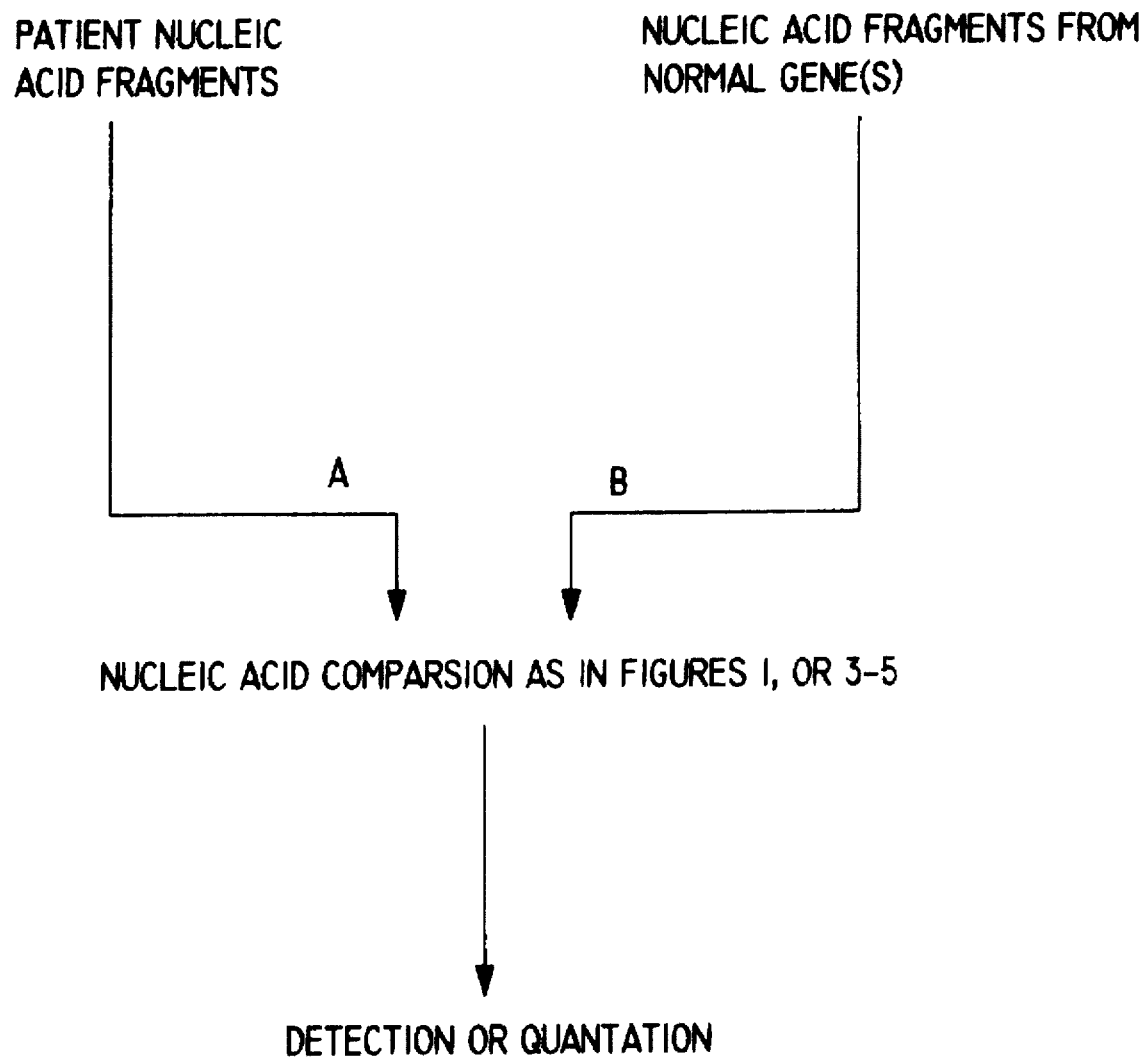
Figure 3:
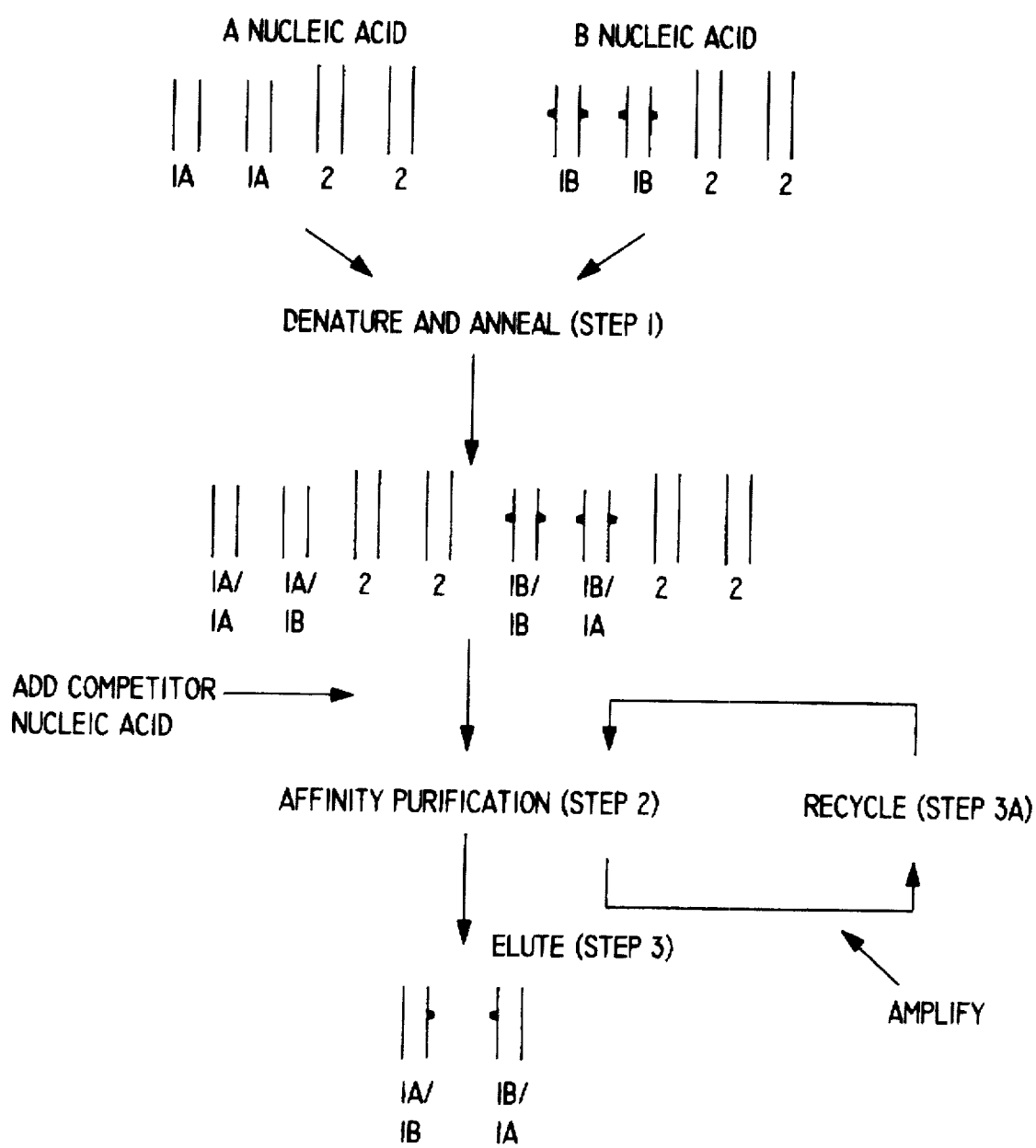
Figure 4:
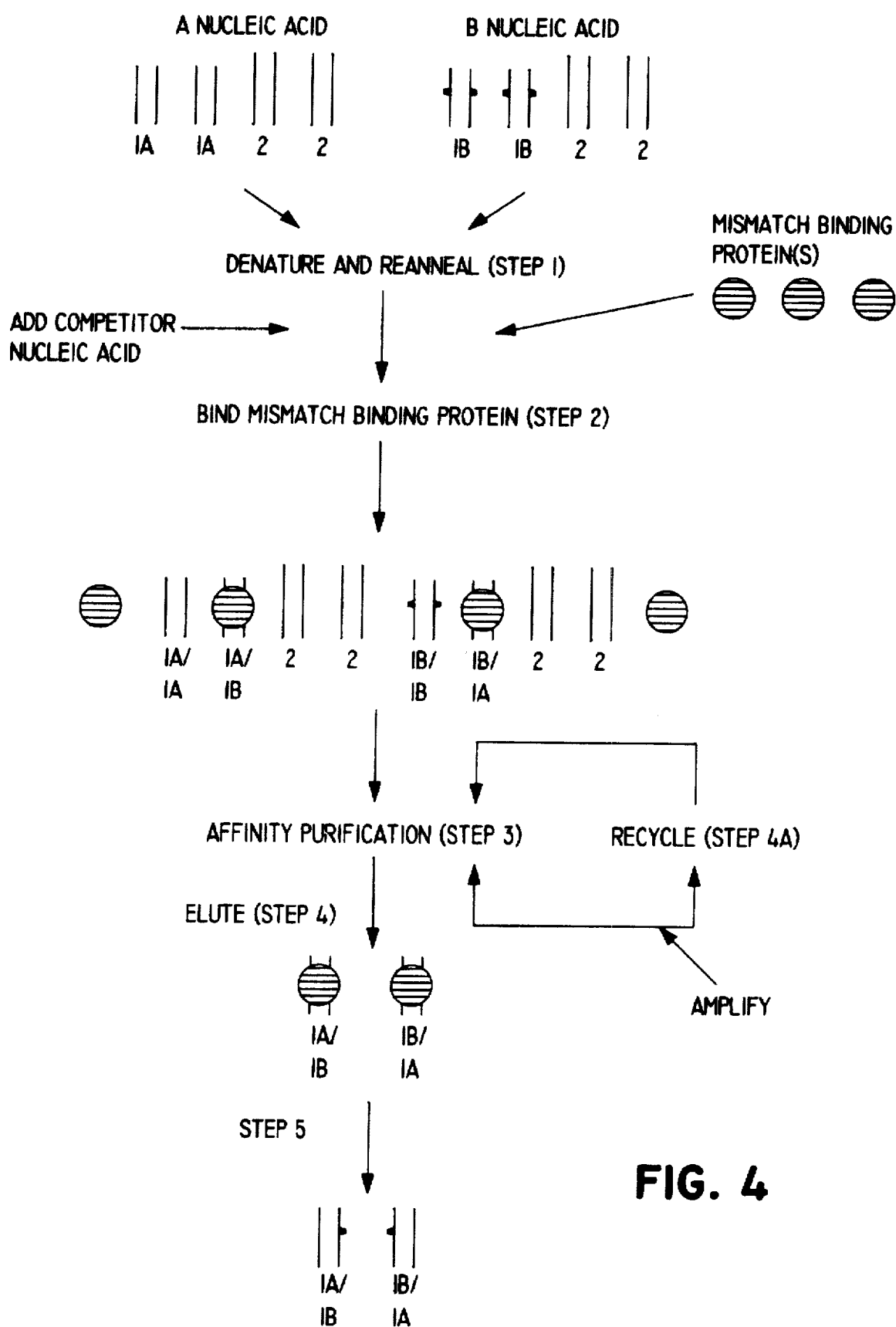
Figure 5:
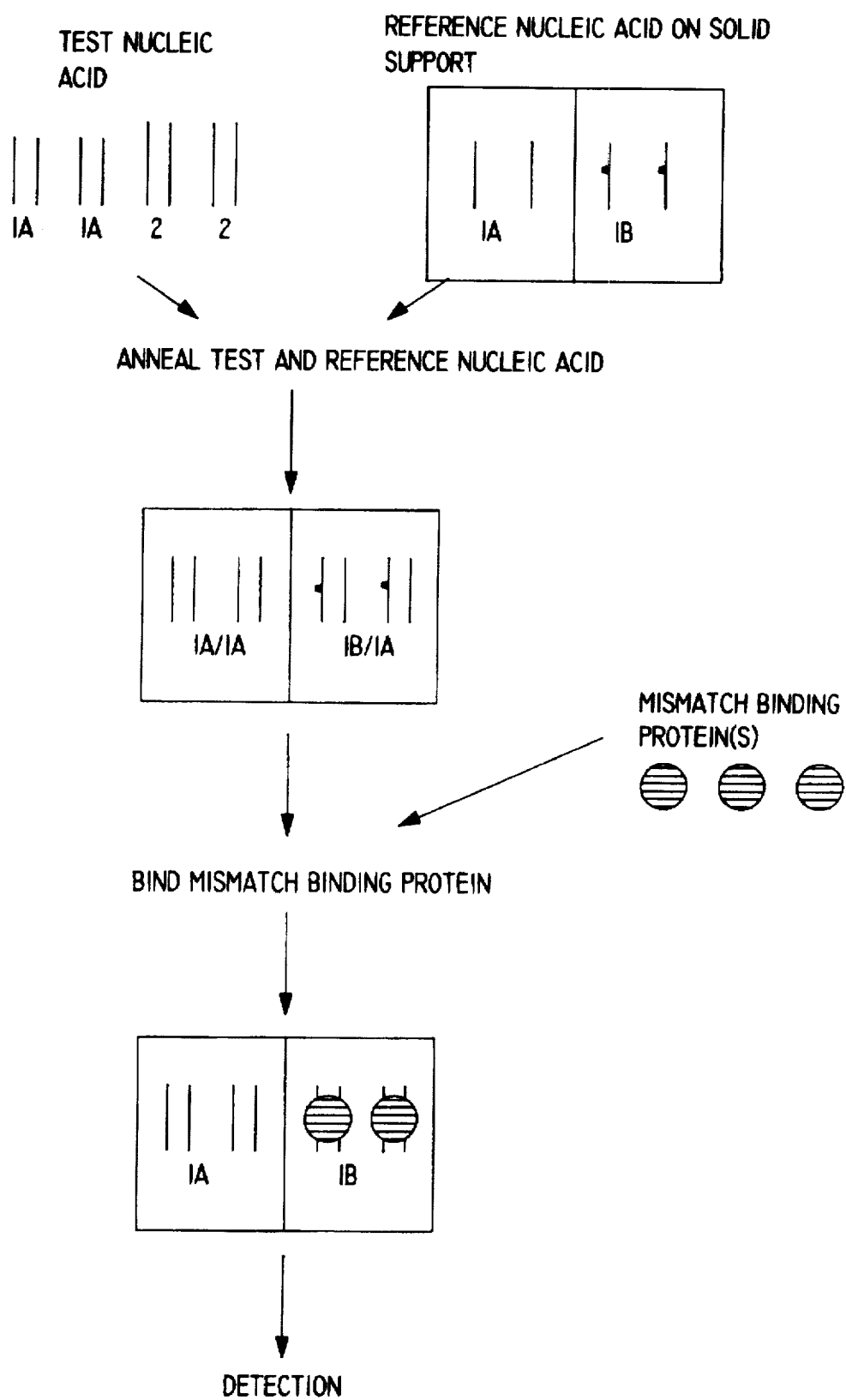
Figure 6:
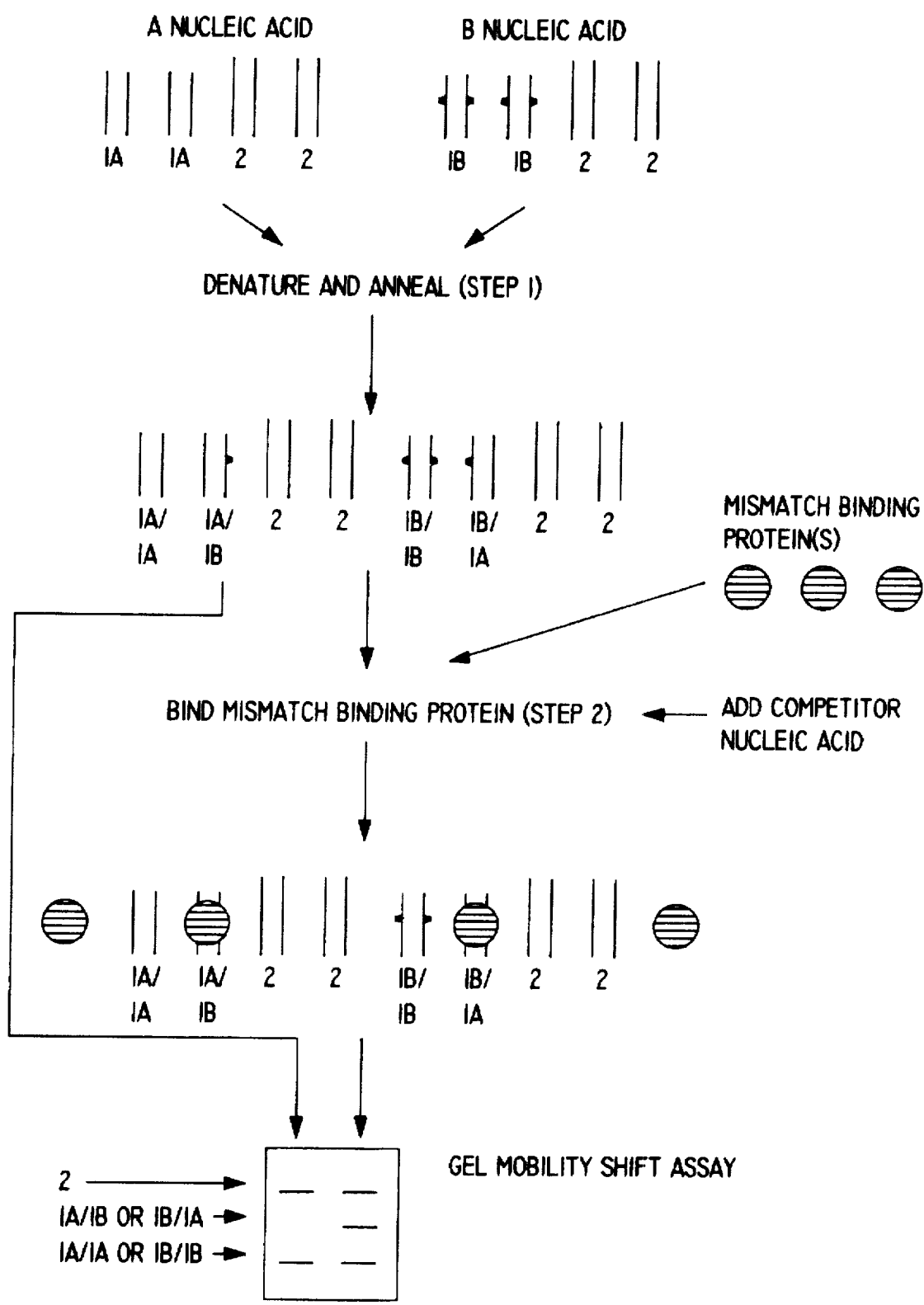
Figure 7:
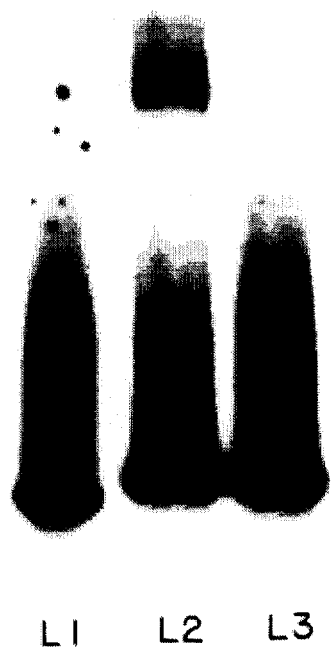

FIG. 1 schematically illustrates a method of detecting nucleic acid sequence mismatches;

FIG. 2 schematically illustrates a method for performing genetic disease diagnosis using a method of the invention in which the reference nucleic acid is labeled or detected using other means;

FIG. 3 schematically illustrates a method of affinity purifying heteroduplex nucleic acid molecules using a mismatch binding protein;

FIG. 4 schematically illustrates heteroduplex affinity purification in which heteroduplex mismatch binding protein complexes are fractionated;

FIG. 5 schematically illustrates a method of detecting nucleic acid sequence mismatches using an array of plural, separate reference nucleic acids arranged on a solid support;

FIG. 6 schematically illustrates a method of detecting nucleic acid sequence mismatches using a band shift assay;

FIG. 7 illustrates the results of a band shift assay; and

Figure 8:
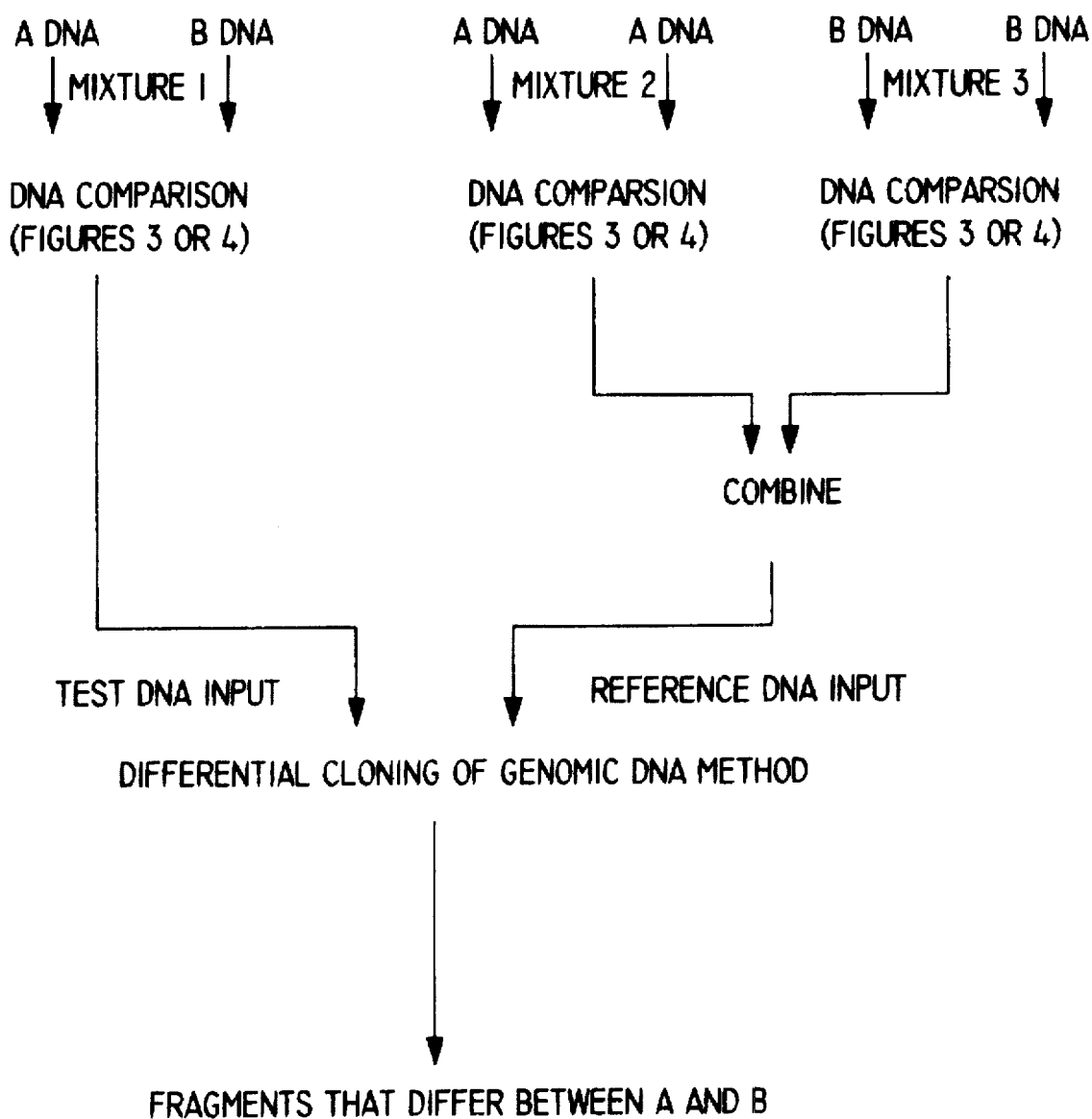

FIG. 8 schematically illustrates a method of differentially cloning nucleic acids sequences containing sequence variations.

Figure 9:
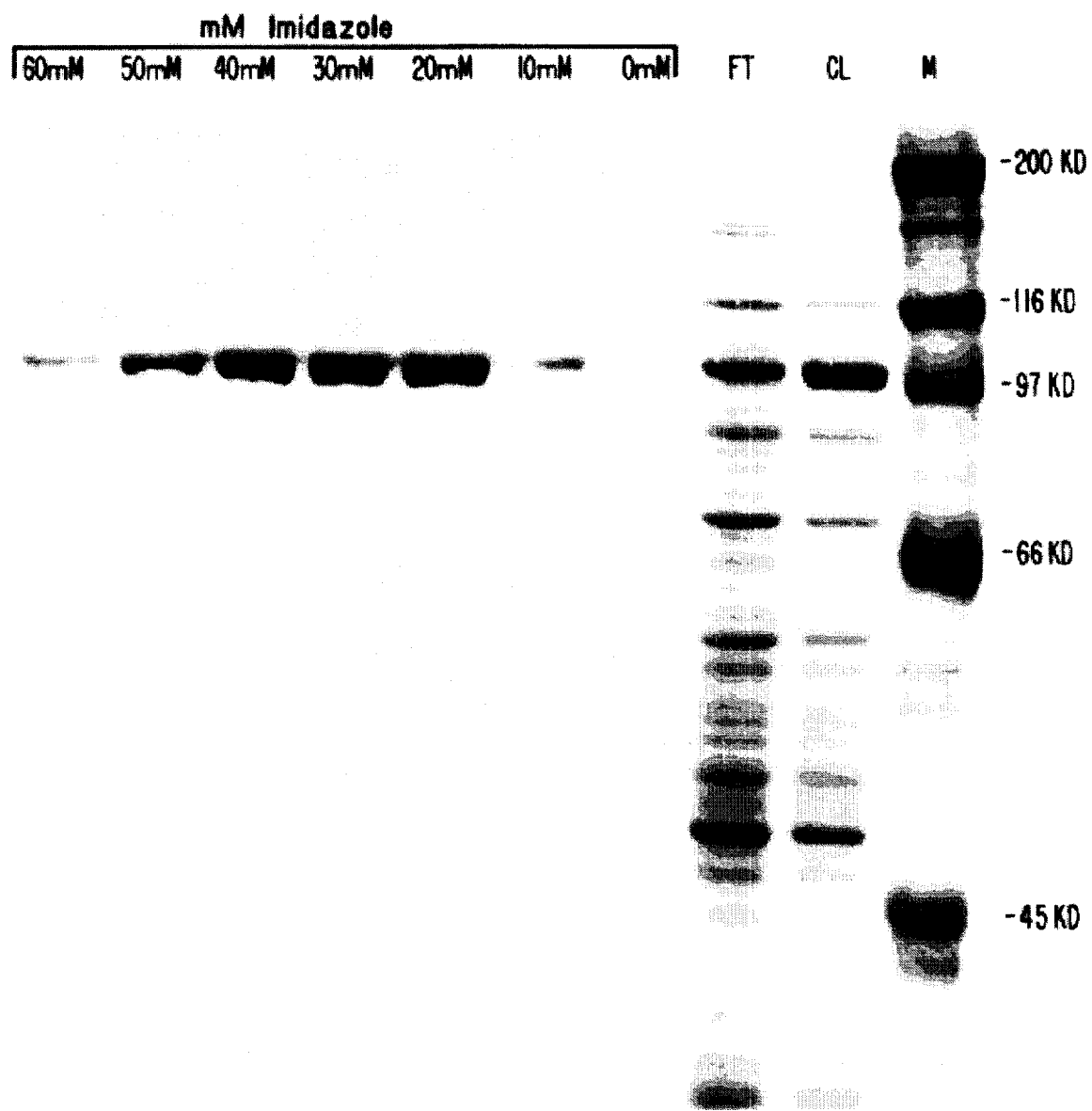

FIG. 9 is a polyacrylamide gel showing the results of purification of histidine-tagged MutS.

Figure 10:
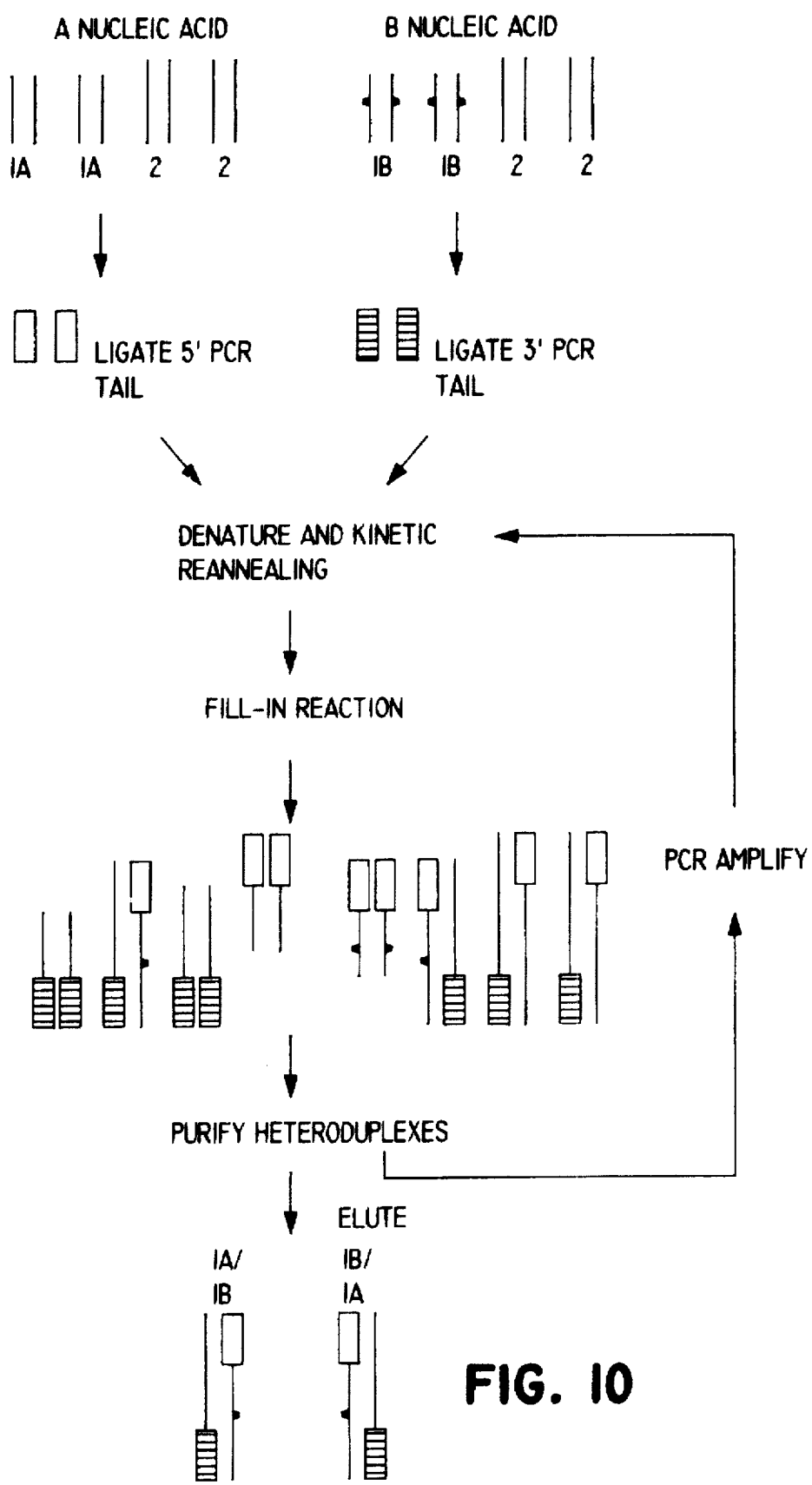

FIG. 10 schematically illustrates a method of differentially analysing test/reference nucleic acid hybrids containing a mismatch.

We next describe preferred embodiments of the invention.

I. Preparation of Nucleic Acids

Test or reference nucleic acids can be prepared using a variety of techniques. For example, nucleic acid can be extracted from cells and used directly, or a specific region of extracted nucleic acid may be amplified; alternatively, nucleic acid may be synthesized.

Cultured cells, tissue or blood samples may be used as a source or as the source of a nucleic acid sequence. Cultured monoclonal cell lines will give a single type of test nucleic acid, and cultured polyclonal cell lines can be used to check for differences between one standard nucleic acid and a library of nucleic acids containing many different test DNAs. Either chromosomal and/or extra-chromosomal DNA, such as plasmid DNA, can be isolated for use as test or reference nucleic acid.

Nucleic acid can be extracted from cells, purified, and digested with restriction enzyme(s) to create nucleic acid fragments, and also may be subsequently amplified. The polymerase chain reaction (PCR) can be used to amplify a given region of nucleic acid in order to limit the scope of inquiry to this region, by choosing appropriate primers that flank the region of interest. In addition, multiple primers can be used at once to amplify a set of regions of interest for simultaneous comparison.

Test or reference nucleic acid may also be prepared from synthetic DNA. DNA can be synthesized, and one or more oligonucleotides may be used as a test or reference nucleic acid. Oligonucleotides are particularly useful as reference nucleic acid for moderate size regions.

A test or reference nucleic acid may also include a mixture of two or more of cellular DNA, amplified DNA, and/or synthetic DNA, for simultaneous comparison of different nucleic acid loci.

1. Representational Difference Analysis.

If desired, a nucleic acid sample may be treated so as to reduce the complexity of the sample by removing irrelevant or unnecessary nucleic acid sequences, e.g., using representational difference analysis, subtractive hybridization or kinetic enrichment (Kinzler et al., Nucleic Acid Research 17, 10:3645 1989); Lisitsyn et al., Science 259:956 (1993), both references of which are hereby incorporated by reference). The complexity of a nucleic acid sample may be decreased significantly by preparing a representative portion of each of the test and reference nucleic acid samples, or of the denatured and reannealed test/reference sample, as described by Lisitsyn et al., supra. Nucleic acid populations of reduced complexity, i.e., "representations", allow for detection of nucleotide sequences differences between two complex genomes. One method of creating a representative portion of a nucleic acid sample is to selectively amplify certain fragments relative to others. For example, test or reference nucleic acid is first cleaved into restriction fragments, and then PCR tails are ligated onto the ends of the fragments. If the restriction sites chosen for cleavage occur infrequently, then the average restriction fragment size will be large. Upon amplification of the tailed fragments using PCR primers that are complementary to the tail sequences, the smaller fragments of the mixture will be selectively amplified. Thus, a representative nucleic acid sample is created which contains the relevant sequences but is significantly less complex than the original nucleic acid sample. Subsequent reiterations of the method will further enrich the sample for relevant sequences.

Test or reference nucleic acids also may have identical primer sequences incorporated at their ends to permit the later amplification of the heteroduplex nucleic acid; for example, PCR tails may be added onto the ends of, e.g., the "A" and "B" samples in FIG. 1, prior to step 1, and PCR amplification may be performed at a later step in the procedure.

2. Differential PCR Tailing.

PCR also can be used so as to allow subsequent amplification of only test-reference hybrids, and thus reduce the frequency of test-test and/or reference-reference hybrids in the sample. FIG. 10 schematically illustrates this method. It will be appreciated that complete or partial digestion by multiple restriction enzymes yields non-symmetric 5' and 3' ends suitable for differential PCR tail ligation. Of course, the first PCR tail may be ligated onto reference nucleic acid and the second PCR tail may be ligated onto test nucleic acid. According to this method of the invention, only test-reference hybrids will undergo exponential amplification. This method is described in detail below.

3. Differential Strand Labeling.

Test and reference nucleic acids may also be differentially labeled to allow their progress to be traced through the comparison process. For example, a test nucleic acid can be left unlabeled and the reference nucleic acid (or another test nucleic acid) can be, for example, end-labeled with $^{32}$P by a kinasing reaction. Any appropriate labeling method may be used; e.g., to permit detection of radioactively-labeled nucleic acid or chromogenic or chemiluminescent detection of, for example, a biotin labeled nucleic acid. In addition, determining the presence or absence of specific nucleic acid sequences may be achieved by differential detection, e.g., using different PCR primer sequences which are sequence specific for the fragments of interest. The subsequent selection of corresponding primer oligonucleotides for use in the PCR amplification reaction, followed by analysis of the amplified nucleic acid, will give amplification of the selected nucleic acid.

II. Preparation of Heteroduplexes and Homoduplexes

Heteroduplex nucleic acid includes double stranded nucleic acids in which the molecules contain one strand each from the test and reference nucleic acids. If the test and reference nucleic acids contain differences, annealing of test and reference strands will create heteroduplex molecules. Where the test and reference nucleic acids are completely homologous or the test and reference strands anneal as test/test or reference/reference hybrids, a homoduplex will be created. The heteroduplex molecule forms despite the mismatch because the remainder of the matched base pairs stabilizes the heteroduplex molecule. Thus, heteroduplex molecules are formed by fragments that are similar enough to anneal but that contain mismatches.

The degree of similarity necessary for a heteroduplex to be formed can be controlled by the stringency of the annealing conditions. For example, if the annealing reaction is run at an elevated temperature, single stranded molecules will need to have increased sequence similarities before they can form heteroduplexes. Conditions for annealing of nucleic acids to form hybrids are well-known in the art or, if unknown, can be determined by routine experimentation. See, for example, Alt et al. (1978, J. Biol. Chem. 253:1357, hereby incorporated by reference).

A standard method of denaturing and reannealing nucleic acids which may be used to prepare heteroduplexes according to the invention is the following. The test nucleic acid is suspended in 100 ul of 1×SSC buffer (0.15M NaCl, 0.015M Nacitrate) in an eppendorf tube. The tube is placed in a beaker of water, and the beaker of water is placed in a boiling water bath until the water in the beaker boils. After ten minutes of boiling, the beaker is removed from the water bath, and allowed to cool to 65° C., and placed in a 65° C. water bath. The 65° C. water bath is switched off. The nucleic acid is allowed to anneal during cooling of the 65° C. water bath to room temperature. The nucleic acid can then be ethanol precipitated and resuspended in TE buffer.

III. Identification of Heteroduplex Fragments

FIGS. 1–6 and 8 schematically illustrate methods for the detection and/or analysis of genetic differences according to the invention. FIG. 7 shows the results of one such identification.

In FIG. 1, a method of detecting a nucleotide pair mismatch is shown schematically. In step 1, test and reference nucleic acids (samples A and B, respectively, each sample containing two different nucleic acid fragments, 1 and 2, respectively), are denatured and reannealed such that single stranded molecules from sample A nucleic acid and sample B nucleic acid reanneal to form duplexes. Fragment 2 in each of the test and reference samples is identical (i.e., contains no mismatches), and forms a homoduplex after the reannealing process. In contrast, fragment 1A differs from fragment 1B by only a single base pair mismatch. When a single strand of fragment 1A reanneals with a single strand of fragment 1B, a heteroduplex nucleic acid molecule forms ("1A/1B" in the figure) containing a mismatched base pair. This is shown schematically in FIG. 1 as the mixture of denatured and reannealed fragments between steps 1 and 2. Fragments 1A/1B and 1B/1A each contain a nucleotide pair mismatch, whereas fragments labeled "1A/1A", "1B/1B", and "2" are fully complementary. The mixture of fragments is then subjected to a binding reaction in which the mismatch binding protein is allowed to bind to fragments containing mismatches. The results of the binding reaction are shown schematically in step 2 of FIG. 1, in which the protein is shown bound to each of fragments "1A/1B," and "1B/1A" containing mismatches. In step 3, the mismatches are detected and/or quantitated. Examples of detection and quantitation of nucleotide pair mismatches are disclosed herein. Optional steps in the method shown in FIG. 1 and in other figures include the addition of competitor nucleic acid prior to binding of the mismatch binding protein to reduce nonspecific binding to matched nucleic acid, and thus reduce background; and the amplification of a sample containing heteroduplex nucleic acid at some step prior to detection or quantitation. These optional steps are discussed more fully below.

In FIG. 2, a quantitative method of genetic disease diagnosis according to the invention is schematically shown. Patient nucleic acid is prepared according to conventional techniques, and cleaved into restriction fragments. The nucleic acid standard, to which the patient nucleic acid is to be compared, contains "normal" nucleic acid fragments, i.e., nucleic acid fragments having a sequence known to reflect the normal gene functions. In this example, either the nucleic acid standard is labeled or the mismatch binding protein is labeled. The two nucleic acid samples are then subjected to any one of the methods of the invention, including those illustrated in the figures. This step is referred to as "Nucleic Acid Comparison" in FIG. 2. The results of the nucleic acid comparison, i.e., the detection or isolation of hybrid nucleic acid fragments of patient/standard nucleic acid containing one or more nucleotide pair mismatches, may be subjected to quantitative analysis by quantitating the data present in both input and output samples.

In FIG. 3, a method of selectively enriching for nucleic acid hybrids containing mismatches is shown. In this figure, the affinity purification step involves the selectively sequestering of heteroduplex nucleic acid using a mismatch binding protein. Step 1 of FIG. 3 is similar to step 1 of FIG. 1, and involves the denaturation and annealing of a test and a reference nucleic acid sample (A and B, respectively). The mixture of annealed nucleic acid is shown, as in FIG. 1. The annealed mixture is then subjected to an affinity purification reaction in which heteroduplex nucleic acid is bound by a mismatch binding protein under appropriate binding conditions, as described herein. The affinity purification reaction may be an immunoprecipitation reaction in which the mismatch binding protein is allowed to bind to the nucleic acid, followed by immunoprecipitation using an antibody, as described below. Alternatively, the affinity purification reaction may include subjecting the annealed mixture to mismatch binding protein coupled to beads, e.g., in a free slurry or poured into a column matrix. The bound heteroduplex nucleic acid will become sequestered with the beads and will thus be separable from the unbound nucleic acid. After separation, the bound nucleic acid is eluted or released (Step 3). The mismatch binding protein may be attached to any solid support that will permit the separation of free nucleic acid from nucleic acid bound by the mismatch binding protein.

Affinity purification of heteroduplex nucleic acid may involve any of a number of affinity purification techniques, and is not limited to that discussed above. For example, as shown in FIG. 4, the affinity step may involve selectively sequestering of the entire heteroduplex/mismatch binding protein complex, rather than just the heteroduplex nucleic acid itself. Steps 1 and 2 of FIG. 4 are similar to steps 1 and 2 of FIG. 1, in which the annealed mixture is formed and subjected to a binding reaction in which mismatch binding protein binds to heteroduplex nucleic acid in the mixture. In step 3, the heteroduplex/binding protein complexes are selectively retained, e.g., by a matrix to which an antibody specific for the binding protein is coupled. The complexes may then be eluted (step 4), followed by isolation of the heteroduplex nucleic acid (step 5), e.g., by phenol extraction of protein and ethanol precipitation of nucleic acid.

FIG. 5 shows an alternative method of genetic disease screening and diagnosis in which nucleotide pair mismatches are detected in a simple assay. This method is a specific embodiment of that shown in FIG. 1, and involves a solid support in which quantities of reference nucleic acid are spotted onto a membrane in an ordered pattern. The standard (reference) and the patient (test) nucleic acids are then denatured and annealed according to conventional techniques. After the hybrids are allowed to form, the membrane is subjected to a binding reaction in which mismatch binding protein is allowed to bind to any heteroduplexes which may have formed. After unbound mismatch binding protein is washed off the membrane, the presence of bound mismatch binding protein is detected using any appropriate detection technique disclosed herein or known in the art.

An alternative to fixing the reference nucleic acid on a solid support is to fix the test nucleic acid on a solid support. The technique outlined in FIG. 5 can be applied to this alternative method, with the modification that reference nucleic acid is annealed to the fixed test nucleic acid. Methods of fixing test nucleic acid to a solid support include crosslinking, alkaline transfer to a membrane, or other techniques, as described in Ausubel et al., eds., 1992, current protocols in Molecular Biology, John Wiley & Sons, New York, also herein incorporated by reference. Alternatively, in situ hybridization, also as described in Ausubel, can be used to directly anneal reference nucleic acid to test nucleic acid that is contained in sectioned cells. Annealing can be optionally performed in the presence of competitor nucleic acid.

Another alternative method of genetic disease screening or diagnosis involves the detection of nucleotide pair mismatches using a band shift assay. FIG. 6 illustrates this method. In steps 1 and 2, the patient (test) nucleic acid is denatured and annealed to reference nucleic acid and allowed to bind to mismatch binding protein, as described in FIG. 1. The bound nucleic acid is then electrophoresed on an agarose gel. This method takes advantage of the decreased mobility of bound heteroduplexes relative to unbound hybrids in agarose. As shown schematically in FIG. 6, the control lane (left), in which the annealed fragments were not subjected to mismatch binding protein, contains only homoduplex fragment 2 (top) and 1A/1A, 1B/1B, or unbound heteroduplex 1A/1B or 1B/1A (bottom), whereas the experimental lane (right) contains both homoduplex bands (top and bottom) and the middle heteroduplex band (1A/1B or 1B/1A). The results of such an assay are shown in FIG. 7. Mismatch binding protein was allowed to bind under binding conditions to a mixture of nucleic acid fragments, and then subjected to agarose gel electrophoresis. The mobility of the nucleic acid fragment in the mixture that contained a nucleotide pair mismatch is near the top of the gel (lane 2) and thus was selectively slowed relative to the faster running unbound nucleic acid fragments, which migrated to the bottom of the gel. The control lanes in FIG. 7 (lane 1 and 3) show that when no mismatch binding protein is added to the binding reaction, there is no binding to fragments and consequently no fragments migrating with the bound fragments in the gel.

A genetic disease may be not only detected, but also further analyzed to learn more about the genetic cause of the disease using the mismatch detection and isolation methods of the invention. Such analysis may include determining the nucleotide sequence of the strands of the isolated heteroduplex nucleic acid, or may involve the cloning of that portion of the patient's nucleic acid that contains the nucleotide sequence difference. FIG. 8 schematically illustrates a method differential cloning of heteroduplex strands. Test nucleic acid includes heteroduplex nucleic acid from samples A and B as shown in FIGS. 3 or 4. This nucleic acid was prepared by annealing a patient and a standard nucleic acid and purifying the heteroduplexes bound by the mismatch binding protein to produce mixture 1 in the figure. Reference nucleic acid in FIG. 8 is prepared from mixtures 1 and 2. Mixture 2 is prepared by denaturing and annealing sample A with itself and purifying heteroduplexes bound by mismatch binding protein. Similarly, mixture 3 is prepared by denaturing and annealing sample B with itself and purifying heteroduplexes bound by mismatch binding protein. Mixtures 2 and 3 are then pooled without denaturing and reannealing again to produce the reference nucleic acid. The test A/B and reference A/A and B/B nucleic acids are then subjected to the differential cloning method described below. This method produces clones of A and B nucleic acids that were part of a A/B heteroduplex.

IV. MutS Binding Reaction

The mismatch binding protein MutS from *Salmonella typhimurium* selectively binds mismatches in heteroduplex molecules. MutS also binds mismatches that include deleted or added bases. Additional mismatch binding factors, such as MutL, can also be used in the binding reaction as an alternative to or in combination with MutS, to increase binding. MutS protein can be purified using the MutS overproducer plasmid pGW1825 (Haber et al., 1988, J. Bacteriol. 170:197) and the method of Su and Modrich (1986, Proc. Nat. Aca. Sci. 83:5057). MutL has been cloned into plasmid pGW1842 (Mankovich et al., 1989, J. Bacteriol. 171:5325), and can be purified using the method of Griley et al. (1989, J. Biol. Chem. 264:1000). Haber et al., 1988, Su et al. 1986, Griley et al., 1989, and Mankovich et al. 1989 are all hereby incorporated by reference.

The mismatch binding protein/heteroduplex binding reaction is typically performed as follows. The reaction is performed in assay buffer (20 mM Tris.HCl pH 7.6, 5 mM $MgCl_2$, 0.1 mM DTT, and 0.01 mM EDTA) for 30 minutes on ice. Typical binding reactions are 10 pmol total volume, with 0.2 pmol of duplex DNA and 40 pmol of mismatch binding protein, e.g., MutS. The addition of ATP to the binding reaction may increase the efficiency of binding of the protein or of cofactors such as MutL.

In addition to selectively binding heteroduplex nucleic acid, MutS nonspecifically binds to homoduplex nucleic acid to some degree. In order to reduce nonspecific binding, competitor (i.e., homoduplex) nucleic acid may be added to the heteroduplex mixture prior to the binding reaction or the affinity fractionation step, as shown in FIGS. 1, 3, and 4. Where the test or reference nucleic acid is labeled, as shown in FIG. 2, the use of excess unlabeled competitor DNA will cause most non-specific binding to occur on unlabeled nucleic acid, as is more fully described below. Thus, the effect of non-specific interactions will be minimized if the label is used to follow the progress of the fractionation. Competitor nucleic acid is also useful in the amplification process. Starting nucleic acid can be prepared with PCR tails to permit amplification, as shown in FIG. 1, step 2. If competitor nucleic acid lacking these PCR tails is added to the mixture prior to amplification, the effect of non-specific interactions will be minimized on PCR amplified heteroduplex nucleic acid because competitor nucleic acid that appears in the heteroduplex mixture will not be amplified.

V. Detection of Nucleotide Pair Mismatches

The detection of heteroduplex nucleic acid according to the invention is accomplished using a binding assay in which one or more mismatch binding protein(s) bind to a nucleotide mismatch to form a nucleic acid/protein complex which is subsequently detected.

For diagnosis of a genetic disease where the mutation that causes the disease is known, the invention provides methods which enable detection of the presence of heteroduplexes between patient and reference nucleic acids. The invention utilizes known methods of nucleic acid hybridization to form duplexes of test and references strands, and provides inventive methods for the sensitive detection of even a single base pair mismatch in a heteroduplex. Thus, a genetic disease, one example of which is sickle-cell anemia, which involves the substitution of a thymine for an adenine at position 17 of the gene sequence encoding the beta chain of hemoglobin, is easily diagnosed by the mismatch detection methods of the invention, as described below. Other diseases involving genetic mutations which are diagnosable according to the invention include the following. For example, Tajima et al. (Jour. Biochem. 105:249, 1989) disclose a gGAG→AAG base change which leads to a Glu→Lys amino acid substitution and results in apolipoprotein E (ApoE) deficiency; Hirshhorn et al. (Jour. Clin. Invest. 83:487, 1989) describe a mutation which leads to adenosine deaminase (ADA)˙ deficiency, i.e., a single base change (CCG→CAG) leading to a Pro→Gln amino acid substitution; Jagadees et al. (Jour. Cell. Biol. Suppl. 13E;291, 1989) describe mutations at seven different locations within the FX gene, GAT→AAT resulting in an Asp→Asn substitution at position 58, GTG→ATG resulting in a Val→Met substitution at position 68, GCC→ACC resulting in a Glu→Lys substitution at position 156, TCC→TTC resulting in a Ser→Phe substitution at position 188, GCC→ACC resulting in an Ala→Thr substitution at position 335, and GGG→AGG resulting in a Gly→Arg substitution at position 447, each mutation of which results in a Factor X deficiency; Ginsburg et al. (Proc. Nat. Aca. Sci. 86:3723, 1989) describes two mutations, GTC→GAC and CGG→TGG resulting in Val→Asp and Arg→Trp substitutions at positions 844 and 834, respectively, each of which produces a defective von Willebrand Factor 2a; Matsuura et al. (Jour. Biol. Chem. 264:10148, 1989) describe a mutation which leads to adenylate kinase deficiency (CGG→TGG) leading to an Arg→Trp amino acid substitution; Dilella et al. (Nature 327:333, 1987) describes a mutation within the PAH gene, tCGG→TGG resulting in an Arg→Trp substitution at position 408, which produces the condition known as phenylketonuria; Bock et al. (Biochem. 27:6171, 1988) disclose a CCT→CTT single base change which leads to a Pro→Leu amino acid substitution and results in antithrombin III deficiency; Ohno et al. (Jour. Neurochem. 50:316, 1988) reports on a CGC→CAC mutation resulting in an Arg→His substitution at codon 178 of the HexB gene which produces Tay-Sachs disease; Gibbs et al. (Proc. Nat. Aca. Sci. 86:1919, 1989) discloses mutations at seven different codons of the HPRT gene, TCT→TTA resulting in a Phe→Leu substitution at position 73, TTG→TCG resulting in a Leu→Ser substitution at position 130, GCA→TCA resulting in an Ala→Ser substitution at position 160, CGA→TCA resulting in premature termination of translation at position 169, TTC→GTC resulting in a Phe→Val substitution at position 198, CAT→GAT resulting in a His→Asp substitution at position 203, and TGT→TAT resulting in a Cys→Tyr substitution at position 205, each mutation of which results in HPRT deficiency; and Vulliamy et al. (Proc. Nat. Aca. Sci. 85:5171, 1988) discloses mutations at seven different positions within the G6PDH gene, GAT→AAT resulting in an Asp→Asn substitution at position 58, GTG→ATG resulting in a Val→Met substitution at position 68, AAT→GAT resulting in an Asn→Asp substitution at position 126, GAG→AAG resulting in a Glu→Lys substitution at position 156, TCC→TTC resulting in a Ser→Phe substitution at position 188, GCC→ACC resulting in an Ala→Thr substitution at position 335, and GGG→AGG resulting in a Gly→Arg substitution at position 447, each mutation of which produces a condition known as G6PDH deficiency.

A spot detection assay may be used to detect mismatches, as shown in FIG. 5 and described above. This method allows for the detection of genetic differences between a nucleic acid standard (a reference nucleic acid) and a number of test nucleic acids. Any number of conventional detection methods well-known to those skilled in the art may be used; e.g., direct detection of, e.g., labeled mismatched binding protein, detection of a fluorescent antibody capable of binding the mismatch binding protein, or detection of an antibody conjugated to an enzyme that reacts with a chromogenic substrate.

Also included in the invention are detection methods based on the use of modified nucleic acid and proteins capable of binding the modified nucleic acid. For example, a modified base may occur as part of a mismatched nucleotide pair, and a mismatch binding protein capable of binding to the mismatched pair containing the modified base may be used for detection.

A band shift assay may also be used to detect bound heteroduplex nucleic acid according to the invention, as described above for FIGS. 6 and 7.

Other detection methods useful in the invention are illustrated by way of FIG. 1. Heteroduplexes are formed in step 1 and allowed to bind to mismatch binding protein in step 2. The heteroduplex/mismatch binding protein complexes may then be separated from free nucleic acid by immunoprecipitating the complexes with an antibody specific for the mismatch binding protein in step 3, e.g., using the method of McKay (supra). MutS polyclonal antibodies can be prepared according to conventional antibody preparation procedures using the following procedure.

Purified MutS is electrophoresed on an 8% polyacrylamide gel. After soaking in water 10 min. to remove the SDS, the gel is stained for 10 min in 0.1% coomassie blue in water, and then destained in water. The MutS band is cut out, chopped up into fine pieces with a razor blade. 1 ml of PBS (137 mM NaCl, 2.7 mM KCl, 4.3 mM $Na_2 7H_2O$, 1.4 mM $KH_2PO_4$, pH 7.3) is added, and the mixture is ground up further by passage through progressively smaller syringes. Rabbits are injected with 500 µg of a mixture of fractions containing the MutS protein. Protein for boosts is prepared in the same way, except that Freunds incomplete adjuvant is used. The rabbits are boosted twice with 100 µg of the MutS fractions, and bled to obtain serum.

The serum is pre-absorbed and used in immunoblotting according to the protocols of Harlow and Lane (1988, "Antibodies, A Laboratory Manual," Cold Spring Harbor Press, CSH, New York), hereby incorporated by reference.

After the immunoprecipitation step, heteroduplex nucleic acid fragments may be optionally isolated for further analysis by performing a phenol extraction to remove the binding protein and anti-binding protein antibody.

Alternatively, other means of detecting bound mismatch binding protein may be used; e.g., the mismatch binding protein itself may be labeled or one strand of the heteroduplex nucleic acid may be labeled and followed into bound nucleic acid, also as described herein. Additional detection techniques are described below as procedures for fractionation; e.g., a mismatch binding protein binding column which binds to mismatch binding protein by virtue of a sequence in the binding protein which is recognized by a moiety on the column.

VI. Affinity Fractionation of Heteroduplexes

The invention also provides for selective enrichment of heteroduplexes within a sample by affinity fractionation of fragments containing mismatches, thereby achieving more sensitive detection of the mismatch(es).

The proportion of heteroduplexes in a sample may be substantially increased using affinity fractionation, as shown schematically in FIG. 3. The mixture containing heteroduplexes is subjected to affinity purification, in which the heteroduplexes are bound to and subsequently eluted from a solid support to which mismatch binding protein is coupled. In FIG. 4, the heteroduplex/mismatch binding protein complexes are selectively retained by a matrix to which any moiety is coupled which can bind the complex, e.g., a binding protein specific- or complex specific-antibody.

In addition to antibody supports in which the antibody binds directly to the mismatch binding protein or the nucleic acid/mismatch binding protein complex, other affinity supports may be used. For example, one can take advantage of the ability of a metal, e.g., nickel, column to bind to histidine residues in a polypeptide using immobilized metal affinity chromatography. A histidine tail, e.g., six histidine residues, may be covalently linked to the amino terminus of the mismatch binding protein, as described by Hochuli et al. (November 1988, Biotechnology, p. 1321, hereby incorporated by reference). When the heteroduplex/binding protein complex is applied to a nickel column, the histidine portion of the binding protein will be bound by the column. This procedure is also described in Holuchi et al. (ibid).

A histidine-tagged MutS protein may be prepared according to the following procedure. This procedure describes the preparation of a His-MutS protein in which six histidine residues have been added to the amino terminus of the MutS protein. Of course, other His-MutS proteins may be prepared; for example, any desired number of histidine residues may be added to the amino terminus of the MutS protein, provided the resultant His-tagged MutS protein retains its biological activity in binding mismatched nucleic acid and is retainable on a nickel column. If desired, the His-MutS protein can be purified further using a 20 mM–120 mM phosphate gradient on a hydroxyapatite column or on other protein purification known in the art.

Briefly, six histidine residues may be added to the amino terminus of the MutS protein. The MutS gene may be PCR amplified from plasmid DNA containing the gene using PCR primers which anneal to each end of the gene and prime DNA replication. The amplified DNA is then digested with restriction endonucleases to generate a restriction fragment containing MutS-encoding DNA. The MutS-encoding restriction fragment is then cloned into a polylinker site of a plasmid which allows for expression of the inserted DNA by placing the inserted DNA under control of a promoter. Preferably, this promoter is controllable so that MutS gene expression is initiated at a desired point in the cell cycle; e.g., the inducible *E.coli* lac promoter is useful in an *E.coli* host. The muts-encoding clone is then transformed into an appropriate host strain, and a clone is isolated containing MutS-encoding DNA.

The MutS-encoding clone is grown under conditions which do not allow for expression of the MutS gene until a desired optical density of the cell culture is reached. The culture is then induced to produce His-MutS, and the cells grown until they are harvested. The cells are then centrifuged, and the pellets are frozen at −80° C. until ready for use. MutS protein is then purified from the cell pellet as follows. The cell pellet is thawed on ice and resuspended in lysis buffer (20 mM KPO4 pH 7.4, 10 mM betamercaptoethanol, 0.5M KCl, 1 mM PMSF, 200 µg/ml lysozyme). The cells are then disrupted by sonication in an ice water bath. Cell debris is then eliminated by centrifugation at 30,000 rpm for 30 min. The supernatant is filtered through a 0.45 micron filter and applied to a Qiagen (Chatsworth, Calif.) nickel column at a rate of approximately 0.5 ml/min. The column is pre-equilibrated with Buffer D (20 mM KPO4 pH 7.4, 10 mM betamercaptoethanol,) 0.5M KCl, 1 mM PMSF). The column is then washed with 75 ml of Buffer D, followed by another 10 ml of Buffer D containing 10 mM imidazole. The protein was eluted with 80 mM imidazole in Buffer D. The recovered protein is then dialyzed against dialysis buffer (20 mM KPO4 pH 7.4, 10 mM betamercaptoethanol, 0.5M KCl, 0.1 mM EDTA). The MutS protein containing an amino terminal histidine tail is then ready for use.

Another example of an affinity support is an antibody-bound support in which the antibody recognizes and binds to a flag sequence, i.e., any amino acid sequence (e.g., 10 residues) which the antibody specifically binds to. The flag sequence may be engineered onto the amino terminus of the mismatch binding protein. When the heteroduplex/binding protein complex is applied to the antibody column, the antibody will bind to the flag sequence in the binding protein and thus retain the complex. One embodiment of this technique, known as The Flag Biosystem, is commercially available from International Biotechnologies, Inc. (New Haven, Conn.). Larger flag sequences may be also used, e.g., the maltose binding protein, as described by Ausubel et al., 1992, supra.

Alternatively, or in addition to the first fractionation step, the eluted heteroduplex nucleic acid is then recycled one or more times through another affinity binding reaction to refractionate the eluted heteroduplexes and thus remove any remaining non-specifically bound and subsequently eluted homoduplex nucleic acid. The refractionated heteroduplexes are then also subsequently eluted.

Other embodiments of affinity fractionation which are within the scope of the invention include amplification of annealed sample nucleic acid and the addition of competitor nucleic acid, as shown in the figures. For example, the sample nucleic acid may be amplified by PCR after the first affinity binding step, but before the refractionation step. Thus, the bound and eluted heteroduplexes will be amplified and repurified on the affinity support. Elution of the repurified sample nucleic acid should yield relatively pure heteroduplex nucleic acid. In addition, excess competitor nucleic acid (i.e., unlabeled where the sample nucleic acid is labeled, or lacking PCR tails where the sample nucleic acid contains PCR tails) may be added to the sample either prior to or after amplification in order to reduce nonspecific mismatch protein binding to mismatched nucleic acid.

Another fractionation method allows for removal of test-test and/or reference-reference hybrids from a sample prior to analysis. As described generally above and in more detail below, this method provides for differential PCR tailing of duplex fragment ends and thus allows for exponential amplification of test-reference hybrids. Thus, a selective reduction is achieved in the frequency of test-test and reference-reference hybrids within a nucleic acid sample.

This technique, shown schematically in FIG. 10, is useful as an intermediate amplification step and can be performed prior to refractionation to limit affinity purification to test-reference heteroduplexes. A conventional PCR amplification reaction is performed using the experimental conditions disclosed in Lisitsyn, supra, such that the test-reference hybrids are the only heteroduplexes to undergo exponential amplification.

In yet another fractionation method useful according to the invention, second-order kinetics of self-association can be used to further enrich sample nucleic acid for fragments that are more prevalent than others (see Wieland et al., 1990, Proc. Nat. Aca. Sci. 87:2720, hereby incorporated by reference). After sample nucleic acid is enriched for fragments that contain base pair mismatches, e.g., using MutS affinity fractionation, as described herein, these MutS-binding fragments can be further enriched for the relevant sequence using kinetic-enrichment.

Kinetic-enrichment is based on the following principle. If a population of nucleic acid fragments containing a target subpopulation enriched X times relative to unenriched fragments in the sample is melted and reannealed so that only a small proportion of double-stranded nucleic acid forms, double-stranded target nucleic acid would be present $X^2$ times relative to the other sequences present as duplex nucleic acid. To visualize this, consider viral sequences present in excess (ten times more) relative to single-copy β-globin sequences. At early stages of self-reannealing, when 5.0% of the viral sequences are reannealed, only 0.5% of the β-globin sequences will be reannealed. The ratio of the viral sequence to the β-globin sequences in the double-stranded DNA will then be 5% of 10 to 0.5% of 1 (i.e., 100-fold more).

The kinetic-enrichment technique is useful according to the invention as follows. Sample nucleic acid is prepared by combining test and reference nucleic acids under denaturing and reannealing conditions. The sample is then enriched for heteroduplexes thus formed, e.g., by MutS affinity fractionation, as described herein. The MutS-bound heteroduplexe are then teleastd, and the heteroduplex sample kinetically enriched, e.g., is again subjected to denaturation and annealing so that only a small proportion of the sample forms duplexes. Duplexed nucleic acid is then selected as described herein. Because duplex formation will occur at a much higher rate for those fragments that were enriched in the original sample (see Lisityn, supra), the technique serves to further enrich the sample for these fragments.

The fractionation procedure allows for a reduction in the number of homoduplexes in the mixture in the bound fraction; consequently, in the detection or analysis steps, there will be fewer non-specific binding interactions between the mismatch binding protein and homoduplex nucleic acid. The sensitivity of detection and/or quantitation of heteroduplex nucleic acid in a test sample may be further increased by refractionating the eluted sample, or by refractionating the flow-through fractions through repeated affinity steps in which heteroduplexes present either in the eluate or flow-through are selectively retained on the solid support.

After each refractionation binding reaction, bound heteroduplex nucleic acid is eluted and subsequently applied to a fresh or regenerated support. Alternatively, the support may contain a vast excess of binding sites, thus making intermediate elution steps unnecessary.

The solid support useful in the invention may be any one of a wide variety of supports, and may include but is not limited to, synthetic polymer supports, e.g., polystyrene, polypropylene, substituted polystyrene, e.g., aminated or carboxylated polystyrene, polyacrylamides, polyamides, polyvinylchloride, etc.; glass bead, agarose; cellulose, or any material useful in affinity chromatography (see Pharmacia LKB Biotechnology Products Catalog, 1992, Piscataway, N.J., hereby incorporated by reference). The supports may be provided with reactive groups, e.g. carboxyl groups, amino groups, etc., to permit direct linking of the protein to the support. The mismatch binding protein can either be directly crosslinked to the support, or proteins (e.g., antibodies) capable of binding the mismatched binding protein or the nucleic acid/binding protein complex can be coupled to the support.

For example, if the support includes sepharose beads and the mismatch binding protein is coupled to the beads, the binding protein coupled-beads are packed into a column, equilibrated, and the column is subjected to the nucleic acid sample. Under appropriate binding conditions, the protein that is coupled to the beads in the column retains the nucleic acid fragments or the protein/nucleic acid complex which it recognizes. The column is then washed of unbound nucleic acid, and the bound nucleic acid fragments or protein/ nucleic acid complexes are eluted according to conventional techniques known in the art, e.g., using a solution containing salt (e.g., KCl), detergent or imidazole, that reduces the binding between the nucleic acid and protein on the support or the protein/nucleic acid complex and the support; e.g. see Scopes, Protein Purification: Principles and Practice, 1982, Springer-Verlag, New York, or Ausubel, 1992, Current Protocols, supra, both of which are hereby incorporated by reference). Conditions for binding and elution of heteroduplex nucleic acid or heteroduplex/binding protein complexes are typically identical to the conditions described herein for the mismatch binding protein/heteroduplex binding reaction.

The protein may be linked to the support by a variety of techniques including adsorption, covalent coupling, e.g., by activation of the support, or by the use of a suitable coupling agent or the use of reactive groups on the support. Such procedures are generally known in the art and no further details are deemed necessary for a complete understanding of the present invention. Representative examples of suitable coupling agents are dialdehydes, e.g., glutaraldehyde, succinaldehyde, or malonaldehyde; unsaturated aldehyde, e.g., acrolein, methacrolein, or crotonaldehyde; carbodiimides; diisocyanates; dimethyladipimate; and cyanuric chloride. The selection of a suitable coupling agent should be apparent to those of skill in the art from the teachings herein.

Any method that permits the purification of protein/ nucleic acid complexes away from free nucleic acid may be used, e.g., at steps 3–5 of FIG. 4. Methods of affinity purification of mismatch binding protein/heteroduplex complexes include immunoprecipitation. See Ausubel, 1992, Current Protocols, supra, and Harlow et al., 1988, Antibodies: A Laboratory Manual, supra. Alternatively, antibodies to the mismatch binding protein/heteroduplex complex can be attached to any solid support that permits the washing away of free nucleic acid. Alternatively, immobilized metal affinity chromatography may be used to purify histidine-tailed mismatch binding protein that is bound to heteroduplexes.

Additional forms of affinity purification of mismatch binding protein/heteroduplex complexes include the use of nitrocellulose filters that bind protein but not free nucleic acid, or the use of a gel electrophoresis mobility shift nucleic acid-binding assay, both of which are described in Ausubel (1992, supra). For example, the method of the invention shown schematically in FIG. 4 may include a gel mobility shift assay at step 2 of the procedure. Nucleic acid fragments that are bound by mismatch binding protein are identified by their mobility shift. The identified fragments are isolated (steps 4 and 5) by excising them from the gel, and purifying them away from the gel material, as described in Ausubel.

VII. Utilization of Heteroduplexes

The inventive methods disclosed herein allow for recovery of nucleic acid fragments containing nucleotide sequence mismatches. Described below are some of the ways in which these recovered fragments may be used. For example, a recovered heteroduplex sample may be used to determine the identity and position of the mismatch by determining the nucleotide sequence of the mismatch region and comparing the sequence with sequence data from reference nucleic acid. Other examples of ways to utilize the isolated heteroduplexes are as follows.

Heteroduplexes may be used to quantitatively determine the fraction of heteroduplex fragments in a mixture and the proportion of mismatch binding protein bound to heteroduplex nucleic acid, and thus may be used to determine the number of fragments containing mismatches within a sample. Labeling of the input test or reference nucleic acids allows for quantitation of label in both the input and output affinity fractionated samples (FIG. 2). Thus, the amount of label present in the output sample may be used to quantitate the number of heteroduplexes relative to the known amount of labeled input sample.

Labeling of the mismatch binding protein (e.g., with $^{35}$S-methionine) also allows for detection and optional quantitation of the fraction of heteroduplex fragments in a mixture. For example, as shown in FIG. 5, one method includes immobilizing reference nucleic acid on a solid support, such as a membrane, hybridizing of the immobilized reference nucleic acid to test nucleic acid, exposing the membrane to mismatch binding protein under binding conditions such as those specified herein, and then washing away free mismatch binding protein. Alternatively, test nucleic acid may be immobilized to the support and hybridized to free reference nucleic acid prior to binding.

In addition, a moiety that permits affinity purification of nucleic acids can be used to modify the test or reference nucleic acids for detection; e.g., biotin. After the mixture of modified (e.g., biotin-labeled) nucleic acids is exposed to the mismatch binding protein, the mixture may then be selectively enriched for the nucleic acid/binding protein complexes by affinity purification. During this step, the free nucleic acid and free mismatch binding protein will be washed away. Once the nucleic acid mixture has been separated from free mismatch binding protein, the amount of label present in the bound nucleic acid sample may be used to quantitate the number of heteroduplexes in the mixture. Similarly, the amount of label present in the bound protein may be used to determine the number of mismatches present in the mixture. Alternatively, instead of labeling the mismatch binding protein, other methods for detecting the presence of the mismatch binding proteins can be used for quantitation of mismatches, such as an enzyme-linked immunoassay.

If the goal of the genetic screening method is to identify not only the presence of a nucleotide sequence mismatch between test and reference nucleic acids, but also to determine the nature and location of the mismatch, then the affinity purified heteroduplex nucleic acid can be cloned and sequenced to determine the precise sequences and sequence differences between the test and reference nucleic acids. For example, in the genetic disease hemophilia is caused by many different mutations in a 26,000 base region of nucleic acid in the gene encoding blood clotting factor VIII. Thus, it is not possible to diagnose the disease by identifying a known mutation. However, it is possible to detect the many possible mutations which may be a cause of hemophilia according to the invention. Other genetic diseases, e.g., Huntington's disease, in which neither the nature or location of the mutation which causes the disease is known, may be both diagnosed according to the invention, and also characterized as to the identity (i.e., the nature and/or location) of the underlying mutation.

Differential cloning of genomic nucleic acid can be used with complex nucleic acid samples to eliminate background heteroduplex molecules; i.e., heteroduplexes that are formed when a sample is annealed with itself due to the presence of non-unique sequences. This technique is illustrated schematically in FIG. 8. For example, if nucleic acid A and nucleic acid B are to be compared for nucleotide sequence differences, and both samples are a complex mixture of nucleic acid, when the two samples are combined, and denatured and reannealed, many heteroduplexes will form which are not the A/B heteroduplexes which it is the goal to identify, i.e., which contain one strand from sample A mutated gene X and the other strand from reference B normal gene X. Instead, background heteroduplexes will form which contain strands of non-unique nucleic acid that anneal because they are largely homologous; i.e., A/A or B/B heteroduplexes. This background problems may be reduced using the differential cloning method described above, as follows.

Heteroduplexes from denatured and reannealed A/A nucleic acid and denatured and reannealed B/B nucleic acid may be combined to form the reference nucleic acid. The test nucleic acid (A/B heteroduplexes) will include A DNA and B nucleic acid that is denatured and reannealed together rather than separately. The reference (A/A and B/B) nucleic acid is dephosphorylated to prevent ligation of unwanted heteroduplexes to dephosphorylated vector nucleic acid, and then combined with test nucleic acid (heteroduplexes of A/B nucleic acid) in a ratio of approximately 100 (reference) to 1 (test). The combined mixture is separated by size on an agarose gel and again denatured and reannealed in the gel. In the reannealing process, unique A/B strands are more likely to reanneal than non-unique strands because the latter are more likely to reanneal with excess reference strands. Cloning of the unique A/B test strands will be highly favored due to the inability of dephosphorylated A/A or B/B DNA to ligate to the dephosphorylated vector. The differential cloning technique may be varied as desired using the knowledge of a person of skill in the art.

Alternatively, instead of using differential cloning of genomic DNA, representational difference analysis (RDA) can be used in FIG. 8 (see Lisitsyn et al., supra).

In some circumstances, the goal of the genetic screening may not be to identify the precise mismatch, but to determine the sizes of heteroduplex nucleic acid in an annealed sample identified as containing heteroduplex nucleic acid. The size of a heteroduplex may be determined by agarose gel electrophoresis of affinity purified duplexes. Once the size of heteroduplex fragments are known, size parameters may be used to map the locations of differences in simple nucleic acid samples, such as plasmid DNA or to map the locations or differences in more complex samples via Southern blotting of heteroduplex nucleic acid. Furthermore, where a region of interest is well-defined or where genetic markers are known, other techniques may be used, e.g., Restriction Fragment Length Polymorphism analysis to analyze heteroduplex nucleic acid.

The purified heteroduplex nucleic acid may be used as a probe-to screen a genomic library for other sequences of interest. The heteroduplex-containing sample may be further purified by affinity fractionating the heteroduplexes, and/or PCR amplifying the annealed mixture or refractionating the affinity purified heteroduplexes, and cloning the heteroduplex molecules.

In addition, any conventional technique for comparing nucleic acids, e.g., denaturing gradient gel electrophoresis, can be used to further analyze the heteroduplex nucleic acid.

When comparing complex nucleic acid samples, it is important to eliminate background; e.g., false positives, or positive signals generated by reannealing of two different regions within the same test nucleic acid sample that contain some homology and some sequence differences. Background can be eliminated by using controls in which the test nucleic acid or reference nucleic acid is denatured and reannealed with itself. Computer-based assistance can be employed to eliminate these artifacts. For example, a computer can be programmed to examine the digitized images from the gel electrophoresis of reannealed test nucleic acid and/or reannealed reference nucleic acid comparisons, and to remove these artifacts from the digitized gels images resulting from a test/reference heteroduplex comparison.

VIII. Detection of Heteroduplex nucleic acid in a Mixture of Excess Competitor nucleic acid The following experiment demonstrates that a test and a reference nucleic acid sequence may be hybridized and a single base pair differences is detectable. In this example, the nucleotide pair mismatch is known, and the procedure results in detection of mutations in a 16-mer substrate. In addition, 16-mer heteroduplex nucleic acid was fractionated from homoduplex (i.e., fully complementary) nucleic acid. A 16-mer homoduplex control was used to ensure that the method did not fractionate matched nucleic acid to the same degree. Both of the fragments were fractionated in the presence of a large amount of (i.e., excess) competitor nucleic acid to ensure the method could detect mismatches in a background of Nucleic acid.

Nucleic acid samples were prepared as follows. The oligonucleotides DG6R (GAT CCG TCG ACC TGC A), DG4R (CTA GGC AGT TGG ACG T) and DG5 (CTA GGC AGC TGG ACG T) were ordered from Operon Technologies (Alameda, Calif.) and separately resuspended in TE buffer to a concentration of 10 pMol/ul. DG6R was kinased with 5000 Ci/mmol $^{32}$P ATP. Lambda ladder DNA from Bethesda Research Laboratories (Bethesda, Md.) was used as a competitor DNA.

Heteroduplexes were created as follows. 8 pmol of the kinased DG6R and 10 pMol of DG4R in 40 ul of assay buffer were placed in a 70° C. water bath for 10 minutes. The water bath was then switch off and allowed to cool to room temperature to allow the oligonucleotides to anneal. The result of this annealing reaction was called DG-4/6 Het. The same annealing reaction was run between DG-5 and DG-6R, and the result of this reaction was called DG-5/6 Hom. DG-4/6 Het. contains a GT mismatch in place of the GC match present in DG-5/6 Hom.

The MutS protein was over produced, as described by Haber (1988, supra), at 42° C. in MM294 mutS::Tn10 cells that carried the lambda cI857 gene on pSE103 (Ellege et al., 1985, J. Bacteriol. 162:777) and the MutS gene on pGW1825 (Haber 1988, supra), all references of which are hereby incorporated. MutS was purified using the method of Su and Modrich (1986, supra). Dilution buffer for MutS includes 0.02M KPO4 pH 7.4/0.05M KCl/0.1 mM EDTA/1 mM dithiothreitol/0.1 mg/ml bovine serum albumin. The purified and concentrated fraction containing MutS was used in the following experiments. MutS polyclonal antibody was also produced according to the method of Haber (1988, supra). The binding of MutS to heteroduplex nucleic acid was performed in assay buffer, as described above.

Affinity fractionation of heteroduplex nucleic acid was performed as follows. Two binding reactions were incubated on ice for 30 minutes, one containing heteroduplex nucleic acid and a control containing homoduplex DNA. The heteroduplex reaction contained 14.5 pMol of MutS, 200 fmol of DG-4/6 Het, and 2 ug of competitor nucleic acid in a total volume of 20 ul. The control reaction contained 14.5 pmol of MutS, 200 fmol of DG-5/6 Hom, and 2 ug of competitor nucleic acid in a total volume of 20 ul. After 30 minutes on ice, 5 ul of anti-MutS antibody was added to each binding reaction, and the result was incubated on ice for 60 minutes. 10 ul of Staphylococcus aureus cells that had been washed twice in assay buffer were added to both binding reactions (see McKay, 1981, supra) and the result was incubated on ice for an additional 30 minutes. Both reactions were then spun in a microfuge for 3 minutes at 4° C. and the pellet was washed 8 times in assay buffer.

The pellet from each binding reaction was counted in a scintillation counter to test for immunoprecipitation of heteroduplex nucleic acid. After normalizing for the total number of counts in each reaction, 53 fold more oligonucleotides precipitated in the heteroduplex reaction than in the homoduplex reaction. Thus, heteroduplexes containing a single base pair mismatch could-be detected after affinity fractionation of a mixture containing excess competitor nucleic acid.

IX. Detection of a Mismatched Nucleotide Pair in a 1 KB Fragment

The invention may be used to identify a single base pair change in a 1 KB region of nucleic acid in the presence of an excess of matched nucleic acid competitor.

DNA samples and heteroduplexes were prepared as follows. Single stranded circular DNA from M13mp8 DNA containing a G to A transition mutation in the unique PstI site (see Loechler, 1984, Proc. Nat. Aca. Sci. U.S.A. 80:6271, hereby incorporated by reference) was denatured and annealed in the presence of linear duplex wild-type M13mp8 DNA to create a heteroduplex (see Kramer et al., 1989, J. Bacteriol. 171:5339, hereby incorporated by reference). The heteroduplex thus formed contained a C-A mismatch in the PstI site, which prevented cleavage of the site by PstI. Control homoduplex DNA was created using the sense and antisense strands of wild-type M13mp8 DNA. The 1 KB AvaII-BglII fragment containing the mismatch was isolated from both the heteroduplex and wild-type homoduplex DNA by gel purification. The resulting homoduplex and heteroduplex fragments were separately phosphatased and end labeled with $^{32}$P ATP. Free ATP was eliminated with spin columns from the labeled heteroduplex and homoduplex 1 KB DNA fragments. Lambda ladder DNA from BRL-was-used as a competitor.

Affinity fractionation of heteroduplex nucleic acid was performed as follows. Two binding reactions were incubated on ice for 30 minutes, one of which contained the mismatched nucleic acid and a control which contained matched nucleic acid. The heteroduplex-containing reaction consisted of 42 pMol of MutS, 7 fmol of the C-A mismatched 1 KB fragment, and 1 ug of competitor nucleic acid in a total volume of 10 ul. The homoduplex reaction contained the same components, but substituted matched nucleic acid for the mismatched heteroduplex nucleic acid. After 30 minutes on ice, 10 ul of anti-MutS antibody was added to each binding reaction, and the result was incubated on ice for 60 minutes. Then 10 ul of SAC cells that had been washed twice in assay buffer were added to both binding reactions, and the result was incubated on ice for an additional 30 minutes. Both binding reactions were then spun in a microfuge for 3 minutes at 4° C., and the resulting pellet was washed 6 times in assay buffer.

The pellet from each binding reaction was counted in a scintillation counter to test for specific fractionation of heteroduplex nucleic acid. After normalization for the total number of counts in each reaction, 9.6 fold more fragments precipitated in the heteroduplex reaction than in the homoduplex reaction. Thus, a mismatch of a single nucleic acid base pair could be detected in presence of a large amount of competitor nucleic acid.

X. Detection of a Mismatched Nucleotide Pair in a Mixture of Nucleic Acid Fragments The invention may be used to detect a single nucleotide pair mismatch in a mixture of nucleic acid fragments, as described below.

A mixture of homoduplex and heteroduplex nucleic acid was prepared from purified PstI+ and PstI− M13mp8 DNA.

The PstI+ DNA is wild-type M13mp8 DNA, which is cleavable by the restriction enzyme PstI when in double-stranded form, while the PstI– DNA is M13mp8 DNA with a single base C to T mutation in the unique PstI site (the second C in the PstI site is the one that is mutated which prevents cleavage by PstI). 75 ug of both PstI– DNA and PstI+ DNA were separately cleaved with the EcoRI and PvuI restriction enzymes in a total volume of 250 ul each. 200 ul of each reaction were combined, phenol/chloroform extracted, ethanol precipitated, and resuspended in 1× SSC in an eppendorf tube. The tube was boiled in a beaker over a hot water bath for 10 minutes, and then left to cool to 65 degrees for 15 minutes, then moved to a 65 degree water bath, which was switched off and left overnight to cool. The sample was run on a 2% agarose gel, and the 159 bp band was excised. The 159 bp fragments were purified from the gel slice and resuspended in TE buffer. The fragments were then labeled with $^{32}$p dATP in a Klenow fill-in reaction. The unincorporated dATP was eliminated with a spin column. The purified DNA included both heteroduplex and homo-duplex nucleic acid.

Mismatch binding protein was bound to the nucleic acid mixture in a total volume of 10 ul consisting of 1 ul of the DNA mixture (19 fMol), 2 ul of the mismatch binding protein MutS (4 ug), and 1 ul of poly dIdC competitor nucleic acid (1 ug). A control reaction was identically prepared except that it did not contain MutS. Binding was performed on ice for 30 minutes. The MutS reaction and the control reaction were electrophoresed on a 6% non-denaturing tris-acrylaminide-EDTA (TAE) gel. 2 uL of a 50% sucrose solution was added to each reaction just prior to gel loading.

FIG. 7 shows results from an autoradiogram of the polyacrylamide gel. In lane 1, the control reaction shows a single 159 bp band, while Lane 2 shows both the 159 bp band arising from the homoduplex component of the DNA mixture and a larger molecular weight shift band corresponding to the heteroduplex component of the mixture. Lane 3 shows another control in which the MutS protein was heated prior to the binding reaction. As the results show, heat denatured MutS does not bind to heteroduplex nucleic acid and thus does not result in a band shift in the gel.

XI. Preparation of Histidine-tailed MutS Protein

A variant of the native Salmonella MutS protein was created that contained six histidines at its amino terminus to facilitate purification of the His-MutS protein or recovery of the His-MutS protein/heteroduplex nucleic acid complex.

The wild type Salmonella MutS gene was PCR amplified from the plasmid pGW1811 using the following primers:

DKG-MUTS5T (SEQ ID NO. 1)
5' CGG AAT TCG CAT CAT CAT CAT CAT CAT ATG AAT GAG TCA TTT GAT AAG G

DKG-MUTS3X (SEQ ID NO. 2)
5' CGC GGA TCC TTA CAC CAG ACT TTT CAG CCG

The amplified nucleic acid fragment was cut with EcoRI and BamHI and cloned into the polylinker site of pUC18, which placed the MutS-encoding DNA under the control of the inducible Lac promoter. The resulting plasmid, called pDKGA1, was used to transform the E.coli strain GW3732 (Haber, 1988 supra).

A clone (GW3732 pDKGA1) was isolated which contained the plasmid pDKGA1. Because the Lac expression system permits a moderate level of basal transcription, some His-MutS protein is produced even under conditions which result in repression of the lac promoter. This low level of His-MutS production results in poor growth of the transformed cells, and the selective pressure can result in loss of the plasmid from the transformed cells. Thus, care was taken to ensure that the culture did not grow to high density under selective conditions. The His-MutS protein was prepared and purified as follows.

Two 1 liter cultures of GW3732 cells containing plasmid PDKGA were grown with shaking at 37° C. to an $OD_{600}$ of 0.75. The cultures were then induced to produce His-MutS by adding 1 mM IPTG. The cells were grown for another two hours, and then harvested by centrifugation to a cell pellet, decanting the supernatant, and freezing the pellets at $-80°$ C.

A 500 ml culture pellet was then defrosted on ice and resuspended in lysis buffer (20 mM KPO4 pH 7.4, 10 mM betamercaptoethanol, 0.5M KCl, 1 mM PMSF, 200 ug/ml lysozyme). The cells were sonicated in an ice water bath. Cell debris was eliminated by centrifugation at 30,000 rpm for 30 minutes. The supernatant was filtered through a 0.45 micron filter and applied to a Qiagen nickel column at flow rate of 0.5 ml/minute. The column was pre-equilibrated with Buffer D (20 mM KPO4 pH 7.4, 10 mM betamercaptoethanol, 0.5M KCl, 1 mM PMSF). The column was washed with 75 ml of Buffer D, followed by another 10 ml wash of Buffer D with 10 mM imidazole. The protein was eluted with 80 mM imidazole in Buffer D. The recovered protein was dialyzed against dialysis buffer (20 mM KPO4 pH 7.4, 10 mM betamercaptoethanol, 0.5M KCl, 0.1 mM EDTA). FIG. 9 is a polyacrylamide gel showing results of histidine-tailed MutS purification using an imidazole gradient. The His-MutS protein appears in the purification near the 97 KD marker. Histidine-tailed MutS produced as described above was shown to be biologically active in selective binding to nucleic acid mismatches as follows.

XII. Selective Purification of Heteroduplex Nucleic Acid Using Histidine-tailed MutS Protein Homoduplex and heteroduplex nucleic acid were prepared as follows. Three oligonucleotides:

SRB-5-G 3' GAC ATC TGA TCC GTC GAC CTG CAG ATG
AAG A 5'                                    (SEQ ID NO. 3)

SRB-3-T 5' CTG TAG ACT AGG CAG TTG GAC GTC TAC
TTC T 3'                                    (SEQ ID NO. 4)

SRB-3-C 5' CTG TAG ACT AGG CAG CTG GAC GTC TAC
TTC T 3'                                    (SEQ ID NO. 5)

were obtained from Operon Technologies (Alameda, Calif.). Each oligonucleotide was resuspended in TE buffer to a concentration of 10 pMol/µl. SRB-3-T was end labeled in a kinase reaction using 5000 Ci/mmol $^{32}$P-ATP.

Heteroduplex nucleic acid was prepared by combining 8 pmol of the kinased SRB-5-G oligonucleotide and 10 pmol of the SRB-3-T oligonucleotide, followed by incubation of the combined oligonucleotides in a 70° C. water bath for 10 minutes. The oligonucleotides were allowed to anneal by switching off the water bath, and allowing it to cool to room temperature. The duplex formed as a result of this annealing reaction was called SRB/HET.

Homoduplex nucleic acid was prepared by combining 8 pmol of the kinased SRB-5-G oligonucleotide and 10 pMol of the SRB-3-C oligonucleotide, and treating the combined oligonucleotides as described above for preparation of heteroduplex SRB/HET. The resultant homoduplex nucleic acid was called SRB/HOM. SRB/HET and SRB/HOM differ in that the heteroduplex nucleic acid contains a GT mismatch in place of a GC match present in the homoduplex nucleic acid.

Affinity fractionation of heteroduplex nucleic acid was accomplished by performing a binding reaction between the duplex nucleic acid and the His-MutS mismatch binding protein prepared as described above. Briefly, two binding reactions were performed, one containing heteroduplex nucleic acid and a control containing homoduplex nucleic acid. The heteroduplex reaction contained 200 fmol of SRB/HET and 100 pMol of His-MutS, and binding was performed on ice for 30 minutes in assay buffer (20 mM rKPO$_4$ pH 7.6, 5 mM MgCl$_2$, 0.1 mM betamercaptoethanol). The homoduplex binding reaction was performed using 200 fMol of SRB/HOM in place of SRB/HET under the same conditions.

Each reaction was added to 100 µl of Ni-NTA (nickel) resin (Qiagen) in a spin column that had been washed in assay buffer. After addition of the reaction mixtures, each spin column was washed six times with assay buffer containing 1% Triton, and bound DNA was eluted with 1M imidazole, pH 7.0. In the case of the SRB/HET DNA, 27% of the DNA was recovered, while in the case of the SRB/HOM DNA, 2% of the DNA was recovered. The results demonstrate that the His-MutS mismatch protein selectively binds heteroduplex nucleic acid, and that the His-MutS/heteroduplex nucleic acid complex may be selectively retained via affinity purification on a nickel column.

XIII. Selective Recognition and Purification of Mutations in the ARC Gene using PCR Amplified Nucleic Acid Heteroduplex and homoduplex nucleic acid were prepared as follows. Plasmids derived from pTA200 containing the wild-type ARC gene and EG36 mutant ARC gene (Vershon et al., Proteins: Structure, Function and Genetics 1:302, 1986, hereby incorporated by reference) were isolated and used in separate PCR reactions to amplify a region of the ARC gene. PCR reactions included 100 ng of plasmid DNA, 60 pmol of both of the primers ARC5-1 and ARC3-5, and standard PCR reaction components (i.e., PCR buffer, thermostable DNA polymerase, 2 mM of each oligonucleotide). The primer oligonucleotides have the following sequences:

ARC5-1 CCG GCG GAT GAA AGG AAT GAG (SEQ ID NO. 6)

ARC3-5 GGC TTC AAC TTT ACG CGC CAA (SEQ ID NO. 7).

PCR reaction products from the wild-type and EG36 plasmids were gel purified on a 1.5% TAE (tris-acrylamide EDTA) gel, and the 200 bp band was isolated from both. The gel-purified 200 bp PCR products derived from the wild-type and EG36 plasmids were named ARC-WT and ARC-EG36, respectively.

A mixture of heteroduplex nucleic acid and homoduplex nucleic acid, ARC-WT/EG36 was created as follows. A total of 500 ng of both ARC-WT and ARC-EG36 were combined in a 50 mM KCl solution and boiled for five minutes in a water bath. The sample was then allowed to cool slowly to room temperature, and then gel purified on a 1.5% TAE gel. The resulting DNA contained both homoduplex nucleic acid and heteroduplex nucleic acid with GT and CA mismatches. The DNA was then kinased with $^{32}$P-ATP, and unincorporated ATP was separated using a spin column.

ARC-WT/WT homoduplex nucleic acid was created as follows. A total of 1000 ng of ARC-WT DNA was suspended in a 50 mM KCl solution and boiled for five minutes in a water bath. The sample was then allowed to cool slowly to room temperature, and then gel-purified on a 1.5% TAE gel. The resulting DNA contained homoduplex DNA that had been reannealed. The DNA was then kinased with $^{32}$p-ATP, and unincorporated ATP was separated using a spin column.

Affinity purification of heteroduplex DNA was performed as follows. A total of 800 fMol of ARC-WT/EG36 was combined on ice with a final concentration of 0.8 uM His-MutS in assay buffer (20 mM KPO$_4$ pH 7.4, 5 mM MgCl$_2$, 0.4 mM A-mercaptoethanol). After incubation for 30 min. on ice, the reaction was added to a spin column of Ni-NTA nickel resin. Before use, the spin column was washed and equilibrated in assay buffer. After the reaction was added to the spin column, the column was washed six times with assay buffer and 1% triton, and eluted with 1M imidazole pH 7.0. An identical affinity purification reaction was performed with ARC-WT/WT. In the case of ARC-WT/EG36, 4% of the DNA was recovered, and in the case of ARC-WT/WT, 2% of the DNA was recovered. The results demonstrate that the His-MutS mismatch protein selectively binds heteroduplex DNA, and that the His-HutS/heteroduplex DNA complex may be selectively retained via affinity purification.

XIV. Selective Recognition and Purification of Amplified Human Nucleic Acid Containing a Genetic Mutation A genetic mutation contained within human nucleic acid may be detected as follows. Nucleic acid encoding wild type and mutant human β-globin sequences may be cloned into plasmids as described by Abrams et al., Genomics 7:463, 1990, hereby incorporated by reference. the plasmid pEGb0c39, described in Abrams et al., contains a naturally occurring C to T mutation in codon 39 of the β-globin gene; the plasmid pEGwt contains the wild-type sequence. These DNA fragments are amplified by performing large scale plasmid preparation of pEGwt and pEGb0c39. Each amplified DNA is then digested with the restriction enzymes NcoI and BamHI, phenol extracted, and ethanol precipitated.

Heteroduplex nucleic acid is then formed as follows. 25 ug of digested pEGb0c39 and 25 ug of digested pEGwt DNA are combined in a 50 ul volume of 50 mM NaCl (β-Het DNA). The sample is then heated to 99° C. for more than 5 min. and allowed to cool slowly to room temperature. The same reactions is performed using pEGwt DNA to form β-Hom DNA. Each of β-Het and β-Hom are then gel-purified as 438 bp NcoI-BamHI fragments. Purified β-Het fragment is called BO/WT DNA and purified β-Hom is called WT/WT DNA.

Affinity fractionation of heteroduplex nucleic acid is performed as follows. Two binding reactions are incubated on ice for 30 minutes, one containing the BO/WT DNA and a control containing WT/WT DNA. The 14 ul binding reactions contain appropriate amounts of DNA and His-MutS protein. Binding is performed in assay buffer (20 mM Tris-Cl pH 7.6, 5 mM MgCl$_2$, 0.01 mM EDTA, 0.1 mM DTT). Each binding reaction is added to 100 ul of nickel resin in a spin column that has been washed in assay buffer. The two spin columns are washed six times, and DNA is eluted with 1M imidazole, pH 7.0.

Other Embodiments

Other embodiments are within the following claims.

It is further anticipated that other kinds of mismatches, such as asymmetric methylation, can be detected with proteins that bind to hemi-methylated nucleic acids, such as methyltransferases, e.g., dam.

I claim:

1. A method of genetic screening for a nucleotide variation, said method comprising:
   (A) providing a test nucleic acid suspected to contain a nucleotide variation and a reference nucleic acid;
   (B) annealing said test and reference nucleic acids under conditions sufficient to produce a mixture comprising a first concentration of heteroduplex and excess homoduplex nucleic acid, wherein said nucleotide variation comprises one member of a mismatched pair in said heteroduplex, wherein said excess homoduplex nucleic acids are generated by reannealing of a first test or reference nucleic acid strand with a fully complementary second test or reference nucleic acid strand;
   (C) fractionating said heteroduplex from said mixture by affinity purification in which a mismatch repair protein immobilized on a solid support binds said mismatched pair in said heteroduplex;

(D) recovering heteroduplex from said affinity purification to produce a heteroduplex sample which contains a second, higher concentration of said heteroduplex; and (E) detecting, as an indication of a genetic variation between said test and reference nucleic acids, the presence of a mismatched nucleotide pair in said sample.

2. A method of enriching a mixture of duplex nucleic acids for heteroduplex nucleic acid, said method comprising:

(A) providing a mixture of nucleic acids comprising a first concentration of a heteroduplex comprising a test nucleic acid strand and a reference nucleic acid strand, and excess homoduplex nucleic acids, wherein said excess homoduplex nucleic acids are generated by reannealing of a first test or reference nucleic acid strand with a fully complementary second test or reference nucleic acid strand;

(B) separating said heteroduplex nucleic acid from said mixture by affinity purification in which a mismatch repair protein immobilized on a solid support binds a nucleotide mismatch in said heteroduplex nucleic acid; and (C) recovering said heteroduplex nucleic acid from said mismatch repair protein to produce a mixture that contains a second, higher concentration of said heteroduplex.

3. The method of claim 2 wherein step B is conducted by forming a complex between said heteroduplex and said mismatch repair protein and separating said complex from uncomplexed duplex.

4. The method of claim 1 wherein said detecting step comprises detecting one of: said mismatch repair protein bound to said heteroduplex, and said heteroduplex bound to said mismatch repair protein.

5. The method of claim 4 wherein said heteroduplex comprises a detectable moiety and said detecting step comprises detecting said detectable moiety.

6. The method of claim 4 wherein said mismatch repair protein further comprises a detectable moiety and said detecting step comprises detecting said detectable moiety.

7. The method of claim 5 wherein said moiety comprises a label, and said detecting step comprises detecting label bindable by said mismatch repair protein.

8. The method of claim 6 wherein said moiety comprises a label, and said detecting step comprises detecting label bindable to said heteroduplex.

9. The method of claim 4 wherein said detecting step comprises forming an immune complex between one of said bound mismatch repair protein or said bound heteroduplex and an antibody.

10. The method of claim 1 wherein said mismatched nucleotide pair is of unknown identity or location, and further comprising the step of determining the identity or location of said mismatched pair.

11. The method of claim 10 wherein said determining step comprises analyzing the nucleotide sequence of said test or reference nucleic acid of said heteroduplex.

12. The method of claim 1 wherein said steps C and D are repeated prior to performing step E.

13. The method of claim 2 or 3 wherein said steps B and C are repeated prior to performing step E.

14. The method of claim 1 wherein after step (D) but prior to step (E), said method further comprises the additional step of amplifying said heteroduplex comprising said mismatched nucleotide pair.

15. The method of claim 14 wherein said test nucleic acid comprises a first PCR sequence and said reference nucleic acid comprises a second PCR sequence.

16. The method of claim 2 or 3 wherein said method further comprises after step (C) the step of amplifying said recovered mixture.

17. The method of claim 16 wherein said test nucleic acid comprises a first PCR sequence and said reference nucleic acid comprises a second PCR sequence.

18. The method of claim 14 wherein said heteroduplex further comprises PCR tails, and said amplifying step comprises performing a polymerase chain reaction.

19. The method of claim 16 wherein said heteroduplex further comprises PCR tails, and said amplifying step comprises performing a polymerase chain reaction.

20. The method of claims 2 or 3 wherein the reference nucleic acid is labeled, said method further comprising the step of, prior to said separating step (B), adding excess unlabeled nucleic acid to said mixture as a competitor, thereby to reduce background.

21. The method of claim 2 or 3 wherein the reference and test nucleic acids comprise PCR tails, and said method further comprises the steps of:

(i) prior to said separating step, adding excess homoduplex nucleic acid lacking PCR tails; and (ii) after said recovering step, amplifying said recovered mixture, thereby to reduce background.

22. The method of claim 2 or 3 wherein said mismatch repair protein comprises a histidine tail.

23. The method of claim 2 or 3 wherein said mismatch repair protein comprises a flag sequence and said solid support comprises an antibody that binds to said flag sequence.

24. A kit for separating a heteroduplex nucleic acid from a mixture of heteroduplex and homoduplex nucleic acids, said kit comprising:

a solid support on which is immobilized, a mismatch repair protein operative to bind a nucleotide mismatch in said heteroduplex; and means for separating said heteroduplex from said mixture.

25. The kit of claim 24 wherein said mismatch repair protein is MutS protein.

26. A kit for separating a heteroduplex nucleic acid from a mixture of heteroduplex and homoduplex nucleic acids, said kit comprising:

a protein that binds a complex comprising an immobilized mismatch repair protein and a heteroduplex, and means for separating said heteroduplex.

27. The kit of claim 24 or 26 further comprising a reference nucleic acid.

28. The kit of claim 24 or 25 wherein said means comprises a buffer suitable for detecting or separating said heteroduplex.

29. The kit of claim 26 wherein said protein capable of binding said mismatch repair protein is immobilized on a solid support.

30. A solid support for preferentially binding heteroduplex nucleic acids, said support comprising:

a mismatch repair protein immobilized on a solid support and operative to bind a nucleotide mismatch in said heteroduplex.

31. The solid support of claim 30, wherein said mismatch repair protein is MutS protein.

32. The solid support of claim 30 or 31 wherein said solid support comprises an affinity matrix.

33. A method of screening for a nucleotide variation, said method comprising:

(A) providing a duplex nucleic acid;

(B) contacting said duplex with a MutS protein immobilized on a solid support and operative to bind a nucleotide mismatch in said duplex; and (C) detecting the binding of said duplex to said immobilized MutS protein as an indication of the presence of said nucleotide variation.

34. A method of screening for a nucleotide variation, said method comprising:
   (A) providing a test nucleic acid and a reference nucleic acid;
   (B) annealing said test and reference nucleic acids under conditions sufficient to produce a mixture comprising a first concentration of heteroduplex and excess homoduplex nucleic acid, wherein said excess homoduplex nucleic acids are generated by reannealing of a first test or reference nucleic acid strand with a fully complementary second test or reference nucleic acid strand;
   (C) fractionating said heteroduplex from said mixture by affinity purification using MutS protein immobilized on a solid support and operative to bind a nucleotide mismatch in said heteroduplex, wherein said MutS protein binds said heteroduplex; and
   (D) recovering said bound heteroduplex to produce a heteroduplex sample which contains a second, higher concentration of said heteroduplex, said recovery of heteroduplex being indicative of the presence of said nucleotide variation.

35. A method of enriching a mixture of duplex nucleic acids for heteroduplex nucleic acid, said method comprising:
   (A) providing a mixture of heteroduplex nucleic acid and homoduplex nucleic acid;
   (B) contacting said mixture with MutS protein immobilized on a solid support and operative to bind a nucleotide mismatch in said heteroduplex, under conditions such that said heteroduplex binds said MutS protein; and
   (C) recovering said bound heteroduplex to produce an enriched heteroduplex sample.

36. The method of claim 33, wherein said contacting step is carried out in the presence of excess homoduplex nucleic acid.

37. The method of claim 33, wherein said nucleotide mismatch is at an unknown location or is of unknown identity.

38. The method of claim 33, wherein said duplex is formed by the annealing of a reference nucleic acid and a test nucleic acid.

39. The method of claim 38, wherein said test nucleic acid is suspected of containing a mutation.

40. The method of claim 38, wherein at least one of said test or reference nucleic acids is isolated from an organism.

41. The method of claim 40, wherein said organism is a human.

42. The method of claim 33, wherein at least one nucleic acid strand of said duplex has been amplified prior to duplex formation.

43. The method of claim 33, wherein said duplex comprises a detectable moiety and said detecting step comprises detecting said detectable moiety.

44. The method of claim 33 wherein said detecting step comprises forming an immune complex between one of said MutS protein or said duplex bound in step (B) and an antibody.

45. The method of claim 33 or 34 wherein said nucleotide mismatch is of unknown identity or location, and further comprising the step of determining the identity or location of said nucleotide mismatch.

46. The method of claim 33, wherein after step (B) but prior to step (C), said method further comprises the additional steps of isolating said duplex complexes and amplifying said duplex comprising said nucleotide mismatch.

47. The method of claim 34, wherein after step (C) but prior to step (D), said method further comprises the additional steps of isolating said duplex complexes and amplifying said duplex comprising said nucleotide mismatch.

48. The method of claim 46 or 47 wherein said duplex further comprises PCR tails, and said amplifying step comprises performing a polymerase chain reaction.

49. The method of claim 33, 34, or 35, wherein said MutS protein comprises a histidine tail.

50. The method of claim 33, 34, or 35, wherein said MutS protein comprises a flag sequence and said solid support comprises an antibody that binds to said flag sequence.

51. The method of claim 33, 34, or 35, wherein said duplex is further contacted with MutL protein.

52. The method of claim 33, 34, or 35, wherein said duplex is further contacted with MutH protein.

53. A kit for detecting a hetero duplex nucleic acid, said kit comprising:
   MutS protein immobilized on a solid support and operative to bind a nucleotide mismatch in said heteroduplex; and
   means for detecting said heteroduplex.

54. The kit of claim 53, wherein said MutS protein is labeled.

55. The kit of claim 53, further comprising a first protein that binds said MutS protein.

56. The kit of claim 55, wherein said first protein is labeled.

57. A kit for separating a heteroduplex nucleic acid from a mixture of heteroduplex and homoduplex nucleic acids, said kit comprising:
   MutS protein immobilized on a solid support and operative to bind a nucleotide mismatch in said heteroduplex; and
   means for separating said heteroduplex.

58. The kit of claim 57, further comprising a protein that binds said MutS protein.

59. The kit of claim 53 or 57, further comprising a reference nucleic acid.

60. The kit of claim 53 or 57, further comprising MutL protein.

61. The kit of claim 53 or 57, further comprising MutH protein.

62. A solid support for preferentially binding heteroduplex nucleic acids, said support comprising:
   MutS protein immobilized on said solid support and operative to bind a nucleotide mismatch in said heteroduplex.

63. The solid support of claim 62, wherein said solid support is chosen from a synthetic polymer support, a glass bead, agarose, cellulose, or sepharose.

64. The solid support of claim 62, wherein, said solid support further comprises immobilized MutL protein.

65. The solid support of claim 62, wherein, said solid support further comprises immobilized MutH protein.

66. The method of claim 1 or 2, wherein said mismatch repair protein is immobilized directly onto said solid support.

67. The method of claim 33, 34 or 35, wherein said MUTS protein is immobilized directly onto said solid support.

68. The kit of claim 24 or 26, wherein said mismatch repair protein is immobilized directly onto said solid support.

69. The kit of claim 53 or 57, wherein said MutS protein is immobilized directly onto said solid support.

70. The solid support of claim 62, wherein said MutS protein is immobilized directly onto said solid support.

* * * * *